(12) United States Patent
Hundley et al.

(10) Patent No.: US 7,747,308 B2
(45) Date of Patent: *Jun. 29, 2010

(54) NON-INVASIVE SYSTEMS AND METHODS FOR THE DETERMINATION OF CARDIAC INJURY USING A CHARACTERIZING PORTION OF A VOXEL HISTOGRAM

(75) Inventors: William Gregory Hundley, Winston-Salem, NC (US); Craig A. Hamilton, Lewisville, NC (US); Kimberly Lane, Advance, NC (US); Tim Morgan, Palmyra, VA (US); Frank Torti, Winston-Salem, NC (US); Ralph B. D'Agostino, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 975 days.

This patent is subject to a terminal disclaimer.

(21) Appl. No.: 11/346,527

(22) Filed: Feb. 2, 2006

(65) Prior Publication Data

US 2008/0004521 A1 Jan. 3, 2008

Related U.S. Application Data

(63) Continuation-in-part of application No. 11/051,304, filed on Feb. 4, 2005, now Pat. No. 7,333,845.

(60) Provisional application No. 60/542,547, filed on Feb. 6, 2004.

(51) Int. Cl.
*A61B 5/05* (2006.01)
*G06K 9/00* (2006.01)

(52) U.S. Cl. .................................... 600/414; 382/131

(58) Field of Classification Search ................ 382/100, 382/128, 129, 130, 131, 132, 133, 134, 154, 382/162, 168, 181, 196, 203, 219, 232, 255, 382/274, 276, 286, 305, 320; 435/7.92; 536/23.2; 600/529, 407, 410, 420, 414
See application file for complete search history.

(56) References Cited

U.S. PATENT DOCUMENTS 7,258,670 B2 * 8/2007 Bardy ..................... 600/529

(Continued)

FOREIGN PATENT DOCUMENTS

WO WO2004/026140 A 4/2004

OTHER PUBLICATIONS

Wassmuth et al., "Subclinical cardiotoxic effects of anthracyclines as assessed by magnetic resonance imaging—A pilot study", American Heart Journal, Jun. 2001, vol. 141, No. 6, pp. 1007-1013, (June.*

(Continued)

*Primary Examiner*—Seyed Azarian
(74) *Attorney, Agent, or Firm*—Myers Bigel Sibley & Sajovec, P.A.

(57) ABSTRACT

Methods, systems and circuits predict cardiotoxicity induced cardiac injury prior to an irreversible state by electronically generating at least one histogram of mean intensities of voxels/pixels in an MRI image of a left ventricle myocardium and electronically determining a likelihood of cardiac injury due to cardiotoxicity based on data from the at least one histogram.

60 Claims, 16 Drawing Sheets

U.S. PATENT DOCUMENTS

| | | | | |
|---|---|---|---|---|
| 7,301,016 | B2* | 11/2007 | Meyers et al. | 536/23.2 |
| 7,333,845 | B2* | 2/2008 | Hundley et al. | 600/407 |
| 7,396,654 | B2* | 7/2008 | Hayes et al. | 435/7.92 |
| 2005/0215883 | A1 | 9/2005 | Hundley et al. | |

OTHER PUBLICATIONS

Hundley et al. "Magnetic Resoance Imaging Determination of cardiac Prognosis" Circulation 106: 2328-2333 (2002).*

"General Principals of Software Validation; Final Guidance for Industry and FDA Staff" U.S. Dept of Health and Human Services, Food and Drug Administration, Center for Devices and Radiological Health, Center for Biologics and Evaluation Research, 47 pages (Jan. 11, 2002).

Bellenger et al. "Reduction in Sample Size for Studies of Remodeling in Heart Failure by the Use of Cardiovascular Magnetic Resonance" *J Cardiovascular Mangn Reson* 2(4): 271-278 (2000) (Abstract).

Bristow et al. "Doxorubicin Cardiomyopathy: Evaluation by Phonocardiography, Endomyocardial Biopsy, and Cardiac Catheterization" *Annals of Internal Medicine* 88: 168-175 (1978).

Cardinale et al. "Myocardial Injury Revealed by Plasma Troponin I in Breast Cancer Treated with High-Dose Chemotherapy" *Annals of Oncology* 13: 710-715 (2002).

Cerqueira et al. "Standardized Myocardial Segmentation and Nomenclature for Tomographic Imaging of the Heart: A Statement for Healthcare Professionals from the Cardiac Imaging Committee of the Council on Clinical Cardiology of the American Heart Association" *Circulation* 150: 539-542 (2002).

Choi et al. "Transmural Extent of Acute Myocardial Infarction Predicts Long-Term Improvement in Contractile Function" *Circulation* 104: 1101-1107 (2001).

Chuang et al. "Importance of Imaging Method Over Imaging Modality in Noninvasive Determination of Left Ventricular Volumes and Ejection Fraction: Assessment by Two- and Three-Dimensional Echocardiography and Magnetic Resonance Imaging" *Journal of the American College of Cardiology* 35(2): 477-484 (2000).

Darty et al. "Nursing Responsibilities During Cardiac Magnetic Resonance Imaging" Department of Internal Medicine (Cardiology Section) and Radiology at the Wake Forest University School of Medicine (no date).

Del Carlo et al. "Cardiac Troponins in Congestive Heart Failure" *American Heart Journal* 138: 646-653 (1999).

Dombernowsky et al. "Doxorubicin and Paclitaxel, a Highly Active Combination in the Treatment of Metastatic Breast Cancer" *Seminars in Oncology* 23(5 suppl 11): 23-27 (1996).

Gehl et al. "Paclitaxel and Doxorubicin in Metastatic Breast Cancer" *Seminars in Oncology* 23(6 suppl 15): 35-38 (1996).

Gerber et al. "Relation Between Gd-DTPA Contrast Enhancement and Regional Inotropic Response in the Periphery and Center of Myocardial Infarction" *Circulation* 104:998-1004 (2001).

Gerber et al. "Accuracy of contrast-enhanced magnetic resonance imaging in predicting improvement of regional myocardial function in patients after acute myocardial infarction", Circulation, vol. 106, No. 9, pp. 1083-1089, (Aug. 27, 2002).

Gianni et al. "Cardiac Function Following Combination Therapy with Taxol (T) and Doxorubicin (A) for Advanced Breast Cancer (ABC)" *Proceedings of ASCO* vol. 17 (1998) (Abstract).

Gianni et al. "Paclitaxel by 3-Hour Infusion in Combination with Bolus Doxorubicin in Women with Untreated Metastatic Breast Cancer. High Antitumor Efficacy and Cardiac Effects in a Dose-Finiding and Sequence-Finding Study" *Journal of Clinical Oncology* 13(11): 2688-2699 (1995).

Gottdiener et al. "Doxorubicin Cardiotoxicity: Assessment of Late Left Ventricular Dysfunction by Radionuclide Cineangiography" *Annals of Internal Medicine* 94(part 1): 430-435 (1981).

Hamilton et al. "Is Imaging at Intermediate Doses Necessary During Dobutamine Stress Magnetic Resonance Imaging?" *Journal of Cardiovascular Magnetic Resonance* 3(4): 297-302 (2001).

Hochster et al. "Cardiotoxicity and Cardioprotection During Chemotherapy" *Current Science* 7: 304-309 (1995).

Hortobagyi "Treatment of Breast Cancer" *The New England Journal of Medicine* 339(14): 974-984(1998).

Hundley et al. "Magnetic Resoance Imaging Determination of cardiac Prognosis" *Circulation* 106: 2328-2333 (2002).

Hundley et al. "Magnetic Resonance Imaging Assessment of the Severity of Mitral Regurgitation: Comparison with Invasive Techniques" *Circulation* 92: 1151-1158 (1995).

Hundley at al. "Relation of Cardiac Prognosis to Segment Location with Apical Left Ventricular Ischemia" *The American Journal of Cardiology* 92: 1206-1208 (2003).

Hundley et al. "Utility of Fast Cine Magnetic Resoance Imaging an display for the Detection of Myocardial Ischemia in patients Not Well Suited for Second Harmonic Stress Echocardiography" *Circulation* 100: 1697-1702 (1999).

Jacobson et al. "Magnetic Resonance Imaging of the Cardiovascular System: Present State of the Art and Future Potential" *JAMA* 259(2): 253-259 (1988).

Jensen at al. "Functional Monitoring of Anthracycline Cardiotoxicity: A Prospective, Blinded, Long-Term Observational Study of Outcome in 120 Patients" *Annals of Oncology* 13: 699-709 (2002).

Judd et al. "Physiological basis of Myocardial Contrast Enhancement in Fast Magnetic Resonance Images of 2-Day-Old Reperfused Canine Infarcts" *Circulation* 92: 1902-1910 (1995).

Kellman et al. "Phase-Sensitive Inversion Recover for Detecting Myocardial Infarction Using Gadolinium-Delayed Hyperenhancement" *Magnetic Resonance in Medicine* 47: 372-383 (2002).

Kim et al. "The Use of Contract-Enhanced Magnetic Resonance Imaging to Identify Reversible Myocardial Dysfunction" *New England Journal of Medicine* 343: 1445-1453 (2000).

Leandro et al. "Cardiac Dysfunction Late After Cardiotoxic Therapy for Childhood Cancer" *The American Journal of Cardiology* 74:1152-1156 (1994).

Lebwhol et al. "New Developments in Chemotherapy of Advanced Breast Cancer" *Annals of Oncology* 10(suppl 6): S139-S146 (1999).

Lipshultz et al. "Late Cardiac Effects of Doxorubicin Therapy for Acute Lymphoblastic Leukemia in Childhood" *The New England Journal of Medicine* 324(12): 808-815 (1991).

Longmore et al. "Dimensional Accuracy of Magnetic Resonance in Studies of the Heart" *The Lancet* pp. 1360-1362 (Jun. 15, 1985).

Lorenz et al. "Normal Human Right and Left Ventricular Mass, Systolic Function, and Gender Differences by Cine Magnetic Resonance Imaging" *J Cardiovascular Magn Reson* 1(1): 7-21 (1999).

Maisel et al. "B-Type Natriuretic Peptide Levels: Diagnostic and Prognostic in Congestive Heart Failure: What's Next?" *Circulation* 150: 2328-2331 (2002).

Martin et al. "Imaging Cardiac Structure and Pump Function" *Cardiac Magnetic Resonance Imaging* 16(2): 135-160 (1998).

McDonagh et al. "Biochemical Detection of Left-Ventricular Systolic Dysfunction" *The Lancet* 351: 9-13 (1998).

Missov et al. "Cardiac Troponin I in Patients with Hematologic Malignancies" *Coronary Artery Disease* 8: 537-541 (1997).

Osoba et al. "Effects on Quality of Life of Combined Trastuzumab and Chemotherapy in women with Metastatic Breast Cancer" *Journal of Clinical Oncology* 20(14): 3106-3113 (2002).

Pagani et al. "Dose-Finding Study of Epidoxorubicin and Docetaxel as First-Line Chemotherapy in Patients with Advanced Breast Cancer" *Annals of Oncology* 10:539-545 (1999).

Pattynama et al. "Left Ventricular Measurements with Cine and Spin-Echo MR Imaging: A Study of Reproducibility with Variance Component Analysis" *Radiology* 167: 261-268 (1993).

Rector et al. "Assessment of Patient Outcome with the Minnesota Living Heart Failure Questionnaire: Reliability and Validity During Randomized, Double-Blind, Placebo-Controlled Trial of Pimobendan" *American Heart Journal* 124: 1017-1025 (1992).

Rehr et al. "Left Ventricular Volumes Measured by MR Imaging" *Radiology* 156: 717-719 (1985).

Rehr et al. "Left Ventricular Volumes Measured by MR Imaging" *Radiology* 156: 717-719 (1985).

Rerkpattanapipat et al. "Clinical Utility of Assessments of Left Ventricular Systolic Function and Coronary Arterial Blood Flow During Pharmacological Stress with Magnetic Resonance Imaging" *Topics in Magnetic Resonance Imaging* 11(6): 399-405 (2000).

Rischin et al. "A Phase I and Pharmacokinetic Study of Paclitaxel and Epirubicin in Advanced Cancer" *Investigational New Drugs* 17: 73-80 (1999).

Saeed M et al., "Reversible and irreversible injury in the reperfused myocardium: differentiation with contrast material-enhanced MR imaging", Radiology, Oak Brook, IL, US, vol. 175, No. 3, pp. 633-637, (Apr. 1990).

Schwartz et al. "Congestive Heart Failure and Left Ventricular Dysfuntion Complicating Doxorubicin Therapy" *The American Journal of Medicine* 82: 1109-1118(1987).

Schwartz et al. "Congestive Heart Failure and Left Ventricular Dysfunction Complicating Doxorubicin Therapy" *The American Journal of Medicine* 82: 1109-1118 (1987).

Sechetem et al. "Measurement of Right and Left Ventricular Volumes in healthy Individuals with cine MR Imaging" *Radiology* 163: 697-702 (1987).

Semelka et al. "Interstudy Reproducibility of Dimensional and Functional Measurements Between Cine Magnetic Resonance Studies in the Morphologically Abnormal Left Ventricle" *American Heart Journal* 119: 1367-1373 (1990).

Shek et al. "Paclitaxel-Induced Cardiotoxicity" *Arch Pathol Lab Med* 120: 89-91 (1996).

Singal et al. "Doxorubicin-Induced Cardiomyopathy" *The New England Journal of Medicine* 339(13): 900-905 (1998).

Slamon et al. "Use of Chemotheraphy Plus a Monocolonal Antibody Against Her2 for Matastatic Breast Cancer that Overrexpresses Her2" *The New England Journal of Medicine* 344(11): 783-792 (2001).

Stratemeier et al. "Ejection Fraction Determination by MR Imaging: Comparison with Left Ventricular Angiography" *Radiology* 158: 775-777 (1986).

Suter et al. "Detection of Anthracycline-induced Cardiotoxicity: Is There Light at the End of the Tunnel?" *Annals of Oncology* 13: 647-649 (2002).

Torti et al. "Cardotoxicity of Epirubicin and Doxorubicin: Assessment by Endomyocardial Biopsy" *Cancer Research* 46: 3722-3727 (1986).

Torti et al. "Weekly Doxorubicin in Endocrine-Refractory Carcinoma of the Prostate" *Journal of Clinical Oncology* 1(8): 477-482 (1983).

Unverferth et al "Early Changes in Human Myocardial Nuclei after Doxorubicin" *Cancer* 52:215-221 (1983).

Vaidivieso et al. "Increased Therapeutic Index of Weekly Doxorubicin in the Therapy of Non-Small Cell Lung Cancer: A Prospective, Randomized Study" *Journal of Clinical Oncology* 2(3): 207-214 (1984).

Von Hoff et al. "Daunomycin-Induced Cardiotoxicity in Children and Adults" *The American Journal of Medicine* 62:200-208 (1977).

Von Hoff et al. "Risk Factors for Doxorubicin-Induced Congestive Heart Failure" *Annals of Internal Medicine* 91: 710-77 (1979).

Wassmuth et al, "Subclinical cardiotoxic effects of anthracyclines as assessed by magnetic resonance imaging—A pilot study", American Heart Journal, Jun. 2001, vol. 141, No. 6, pp. 1007-1013, (Jun. 2001).

Wu et at. "Visualisation of Presence, Location, and Transmural Extent of Healed Q-Wave and Non-Q-Wave Myocardial Infarction" *The Lancet* 357: 21-28 (2001).

International Search Report and Written Opinion dated Oct. 18, 2007 for corresponding PCT application No. PCT/US07/00603.

* cited by examiner 1. basal anteroseptal
2. basal anteroseptal
3. basal inferoseptal
4. basal inferior
5. basal inferolateral
6. basal anterolateral 7. mid anterior
8. mid anteroseptal
9. mid inferoseptal
10. mid inferior
11. mid inferolateral
12. mid anterolateral 13. apical anterior
14. apical septal
15. apical inferior
16. apical lateral
17. apex

Mean voxel intensity

Scan 1

Scan 2

5.8 ⇅ 6.1

2 weeks $r^2 = 0.98$

NON-INVASIVE SYSTEMS AND METHODS FOR THE DETERMINATION OF CARDIAC INJURY USING A CHARACTERIZING PORTION OF A VOXEL HISTOGRAM

RELATED APPLICATIONS AND CLAIM OF PRIORITY

This application is a continuation-in-part of U.S. patent application Ser. No. 11/051,304 filed Feb. 4, 2005, which issued as U.S. Pat. No. 7,333,845, on Feb. 19, 2008, which claims the benefit of priority of U.S. Provisional Patent Application Ser. No. 60/542,547, filed Feb. 6, 2004. The contents of the above applications are hereby incorporated by reference as if recited in full herein.

FIELD OF THE INVENTION

The present invention is related to diagnostics and more particularly to the detection of tissue injury.

BACKGROUND OF THE INVENTION

Cancer treatments typically include radiation and/or chemotherapies. The chemotherapies can include one or a combination of cytotoxic agents and/or antineoplastics such as alkylating agents, nitrogen mustards, nitrosureas, antibiotics, hormonal antagonists or androgens, antiandrogens, antiestrogens, estrogen/nitrogen mixtures, estrogens, gonadotroopin releasing hormones, immunomodulators, and other appropriate therapeutic agents.

Doxorubicin is an anthracycline antibiotic isolated from a soil microorganism. Its anti-tumor effects are related to interactions with the enzyme topoisomerase-2 and production of double strand DNA breaks. In addition, this agent generates intracellular free radicals that are highly cytotoxic. doxorubicin is considered one of the most broadly active antitumor agents. Not only is doxorubicin typically considered an important element in modern therapy of breast, soft tissue sarcomas and other solid tumors, it is thought to be an important element of curative combination chemotherapy for acute leukemia, Hodgkin's disease, non-Hodgkin's lymphoma, and many childhood cancers. Thus, for many individuals with advanced stages of cancer, Doxorubicin serves as an important part of their medical regimen.

Administration of doxorubicin therapy is generally limited in adults and children by a cumulative dose dependent cardiotoxicity. Irreversible cardiomyopathy with serious congestive heart failure can be a significant risk in patients who receive doses in excess of 500-550 mg/m$^2$. Unfortunately, the dose that precipitates congestive heart failure varies widely (ranging from 30-880 mg/m$^2$ in a report of 1487 patients studied over a seven year period). Those subjects with advanced age or mild reductions in left ventricular systolic function at rest (left ventricular ejection fraction [LVEF] $\leq$50%), are at greatest risk. In western industrialized countries, it is typically older subjects with cancer and some degree of underlying heart disease whom often are in greatest need for doxorubicin therapy, but for whom medication may be withheld due to potential cardiotoxicity.

One method for detection of doxorubicin-induced cardiomyopathy is intramyocardial biopsy with concomitant left and right ventricular pressure measurements made during cardiac catheterization. Unfortunately, this method involves an invasive procedure and may not be well suited for repetitive measurements over time. Radionucleotide ventriculography is also widely used to screen those individuals at risk for developing doxorubicin-induced cardiomyopathy. Individuals who develop a reduction in LVEF of 10% or greater or those individuals who have a fall in ejection fraction to lower than 50% during treatment are at greatest risk for developing irreversible cardiotoxicity. While this information is useful as a potential screening technique, for some individuals, the drop observed in LVEF occurs too late to avert the development of irreversible cardiomyopathy. For this reason, the total dose of doxorubicin may be unduly limited for patients receiving chemotherapy. Importantly for many individuals, doxorubicin therapy is often stopped before patients derive maximal benefit of the drug regimen. A noninvasive, widely available method for accurately detecting those individuals who go on to develop cardiotoxicity would have marked clinical utility.

During the past 7 years, investigators have established the utility of MRI for identifying necrotic tissue within the left ventricle in patients sustaining myocellular injury. This technique incorporates the acquisition of gradient-echo pulse sequences with nonselective preparatory radiofrequency pulses after intravenous administration of gadolinium chelates. In regions of myocardial necrosis, heightened signal intensity occurs on images collected 20 minutes after contrast administration that corresponds to expansion of extracellular volume due to myocellular membrane disruption and increased capillary permeability. This methodology has been utilized to identify transmural myocellular necrosis in patients sustaining acute or chronic Q-wave (ST-segment elevation), and subendocardial (non-transmural) injury in patients sustaining a non-Q-wave (non ST-segment elevation) myocardial infarction. The amount of necrosis found during MRI displays an inverse relationship with recovery of systolic thickening after coronary arterial revascularization. The absence of gadolinium hyperenhancement 20 minutes after contrast administration is associated with myocardial viability and subsequent improvement in left ventricular contraction after sustaining a ST-segment or non ST-segment elevation myocardial infarction. Although some felt delayed enhancement techniques may overestimate regions of myocellular necrosis in the acute infarct, recently, a tagging study in animals indicated that delayed enhancement techniques do identify early myocellular necrosis after myocardial infarction (MI). It is believed that, in border zones of infarcts, dead cells may move due to tethering from adjacent live regions.

With MRI, cardiac structure can be imaged and LV function directly assessed with high temporal and spatial resolution. Since acoustic windows do not limit image acquisition, the utility of MRI is high particularly in subjects with a large or unusual body habitus. This heightened clarity of the images allows investigators to perform quantitative measures of LV structure and function with higher precision than that achieved with radionuclide and ultrasound techniques. A 5% change in LVEF in patients with reduced LV function can be detected with 90% power at a p-value of 0.05 with a sample size of 5 patients per group in a parallel study design. Depending upon operator experience, the same 5% change in LVEF requires an echocardiographic assessment of >100 subjects per group in the same study design. Similarly, the heightened spatial resolution (1 mm$^2$ pixel sizes) achieved with delayed enhancement MRI techniques allows for the detection of micro-infarcts that heretofore may have only been appreciated as cardiac enzymatic elevations detected in serum samples, but not visualized with radionuclide or echocardiographic techniques.

In delayed enhancement imaging a contrast agent is administered to a patient and an image is acquired after the contrast agent has had an opportunity to be distributed to area that is to be imaged such that the contrast agent remains in injured tissue but does not remain in healthy tissue. Such delayed enhancement imaging may be used, for example, to identify myocardial infarcts, as the necrotic tissue of the infarct region will retain the contrast agent while the contrast agent will be purged from the healthy tissue. As such, the infarct may appear as a localized region of higher intensity. Conventionally, delayed enhancement imaging may be used to identify localized regions of tissue damage in tissues such as cardiac tissue, brain tissue, nerve tissue or the like.

SUMMARY OF THE INVENTION

Embodiments of the present invention provide methods, systems and/or computer program products for evaluating tissue characteristics including one or more of: (cardiotoxicity-induced) cardiac injury using voxel/pixel histogram data, identification of injured tissue or alteration of the ratios of native tissue components or chemical or anatomical markers, such as shifting the amounts of normal myocytes and fibrotic tissue in the heart, identifying increases in the amount of extracellular components or fluid (like edema or extracellular matrix proteins), or detecting infiltration of tumor cells or mediators of inflammation into the tissue of interest in a patient, such as a human being.

Some embodiments are directed to methods of evaluating actual and/or potential cardiac injury in a patient. The methods include: (a) electronically determining for a plurality of regions of interest in a medical image of a heart, a location of voxels in three-dimensional space and an associated respective measure of intensity for each of the voxels; and (b) electronically evaluating whether there is a likelihood of present or future cardiac injury based on data from the determining step.

In particular embodiments, the evaluating step may consider the number of voxels having a mean intensity that is greater than 1 sigma and less than about 3 sigma and the three-dimensional location of the voxels having the mean intensity of interest. The methods may include identifying injury to cells in the heart prior to cell death and/or automatically determining whether the voxels in the regions of interest are associated with an increased risk of cardiac injury associated with a decrease in heart function.

In some embodiments, the methods may also include: (a) electronically generating a plurality of visual histograms of voxel intensity, one for each region of interest; and (b) detecting whether there is a clustering of voxels having an intensity that is in a range of between about 2-3 sigma in the histograms. The evaluating cardiac injury can consider clustering data from the detecting step.

In particular embodiments, the methods may further include: (a) obtaining at least one CMR image; (b) interrogating at least substantially all voxels within a contiguous series of short axis slice positions spanning an apex to a base in the at least one CMR image and identifying the intensity and x, y and z coordinate of each voxel in three-dimensional space; and (c) generating a non-invasive imaging biopsy of the patient that can identify locations of voxels of similar intensities within the heart Still other embodiments are directed to methods of predicting cardiac injury prior to an irreversible dysfunctional cardiac state. The methods include: (a) electronically generating at least one histogram of mean intensities of voxels/pixels in an MRI image of a left ventricle myocardium; and (b) electronically determining a likelihood of cardiac injury due to cardiotoxicity based on data from the at least one histogram.

The methods may be configured to distinguish cardiac injury associated with myocardial infarct from cardiac injury associated with cardiotoxicity and/or evaluate a likelihood of a future decrement in LVEF due to cardiotoxicity based on data from the histogram.

Embodiments of the present invention can be useful for non-invasively evaluating cardiac injury. Some embodiments may be particularly suitable for evaluating cancer patients before, during and/or after cancer treatments, for cardiac injury associated with cancer treatments such as chemotherapy and/or radiation therapy. Some embodiments of the invention may also be particularly suitable for evaluating patients with cardiotoxicity or cardiac injury associated with and/or arising from other sources such as, for example, drugs used to treat other conditions, as well as chemical exposure (such as ingestion/inhalation of a poison or gas), environmental exposure, insect bites, snake venom, animal bites, viral, staff, or bacterial infections, as well as cardio status due to other disease states, infectious or otherwise, aging, trauma, and the like.

The methods may evaluate a tail portion of the histogram as a predictor of cardiotoxicity and/or evaluate the histograms to determine locations of clusters of voxels of similar intensity.

Some other embodiments are directed to signal processor circuits. The circuits include a signal processor configured to determine a likelihood of cardiac injury due to cardiotoxicity using at least one histogram of mean intensity voxels from an MRI or X-ray CT image of cardiac tissue, wherein the histogram represents percentage versus mean intensity of voxels within a region of interest.

The signal processor may be configured to evaluate a characterizing portion, distribution pattern or lineshape of the histogram to determine the likelihood of cardiac injury due to cardiotoxicity.

Still other embodiments are directed to non-invasive systems for evaluating cardiotoxicity. The systems include: a signal processor in communication with a physician workstation configured to generate at least one histogram of intensity voxels of at least one image of cardiac tissue of a patient and determine the likelihood of cardiac injury due to cardiotoxicity using at least one of a characterizing portion, distribution pattern, or lineshape of the at least one histogram. The intensity voxels are associated with an MRI or X-ray CT image of cardiac tissue, and wherein the histogram represents percentage versus a measure of intensity of voxels within a region of interest.

Some embodiments are directed to computer program products for evaluating cardiotoxicity in a patient. The product includes a computer readable medium having computer readable program code embodied therein. The computer readable program code includes computer readable program code configured to determine a likelihood of cardiac injury associated with cardiotoxicity using a characterizing portion of at least one histogram of a measure of intensity of voxels in at least one cardiac image obtained after administration of a contrast agent to the patient.

Still other embodiments are directed to systems for non-invasively predicting cardiac injury due to cardiotoxicity prior to an irreversible state of cardiac injury associated with clinical dysfunction. The signal processor includes: a signal processor circuit in communication with a display at a physician workstation, the signal processor configured to electronically generate at least one histogram of mean intensities of voxels/pixels in an MRI or CT image and electronically determine a likelihood of cardiac injury due to cardiotoxicity based on data from the at least one histogram.

The signal processor circuit can include a statistical model that is configured to distinguish cardiac injury associated with myocardial infarct from cardiac injury associated with cardiotoxicity and/or the signal processor circuit may be configured to electronically determine a likelihood of cardiac injury is configured to evaluate a likelihood of a future decrement in LVEF due to cardiotoxicity based on data from the histogram.

In certain particular embodiments of the present invention, a characterizing portion or "signature pattern" in a tail portion of a mean voxel and/or pixel intensity histogram can be used to assess the possible presence of and/or potential for global cardiac injury, such as for example, a likelihood of a substantial decrement in LVEF upon a planned or unplanned subsequent or a future exposure to a toxin, such as a chemotherapeutic agent.

A patient evaluation can be carried out by obtaining a first image of tissue including a region of interest from a first acquisition, for example, after administration of a contrast agent to the patient, and obtaining a second image of the tissue including the region of interest during a second, subsequent acquisition, for example, after administration of a contrast agent to the patient. The subsequent acquisition may, for example, be obtained after a period of time to determine if injury has occurred during that period of time.

The global region of interest may include, for example, at least one of heart, blood, muscle, brain, nerve, skeletal, skeletal muscle, liver, kidney, lung, pancreas, endocrine, gastrointestinal and/or genitourinary tissue. A characteristic of the region of interest of the first image and of the second image is determined so as to allow a comparison of the first image and the second image to determine a potential for a change in a tissue characteristic such as may be caused, for example, by a global injury of the tissue of the region of interest. Such a comparison may include, for example, comparison of mean, average characteristics, histogram shape, such as skew and kurtosis, or distribution of intensities within the histogram.

In further embodiments of the present invention, the global characteristic is a characteristic of pixels/voxels of the region of interest that is based on substantially all of the pixels/voxels in the region of interest. The global characteristic may be an average or mean intensity of pixels/voxels in one or more sections, partitions or a region of interest. The tissue in the region of interest may be at least one of cardiac tissue, brain tissue and/or nerve tissue. The first image and the second image may be magnetic resonance imaging (MRI) images.

While certain embodiments of the present invention are described herein with reference to the detection of tissue characteristics, such as global injury in a patient, such as a human, additional embodiments of the present invention may include detection of global injury in vertebrate or invertebrate animals, reconstructed tissue and/or synthetic tissue. Accordingly, certain embodiments of the present invention should not be construed as limited to the detection of global injury in a human patient.

Particular embodiments of the present invention provide methods, systems and/or computer program products for detecting global cardiac injury in a patient. A first cardiac image is obtained after administration of a contrast agent to the patient. A measure of intensity of the first cardiac image is determined and an intensity histogram of voxels/pixels is generated.

In further embodiments of the present invention, the first cardiac image and the second cardiac image are Magnetic Resonance Imaging (MRI) images and/or x-ray Computed Tomography (CT) images. Also, the measure of intensity of the first cardiac image and the measure of intensity of the second cardiac image may be average and/or mean intensity of the respective images.

As will be appreciated by those of skill in the art in light of the present disclosure, embodiments of the present invention may be provided as methods, systems and/or computer program products.

DESCRIPTION OF EMBODIMENTS OF THE INVENTION

Figure 1:
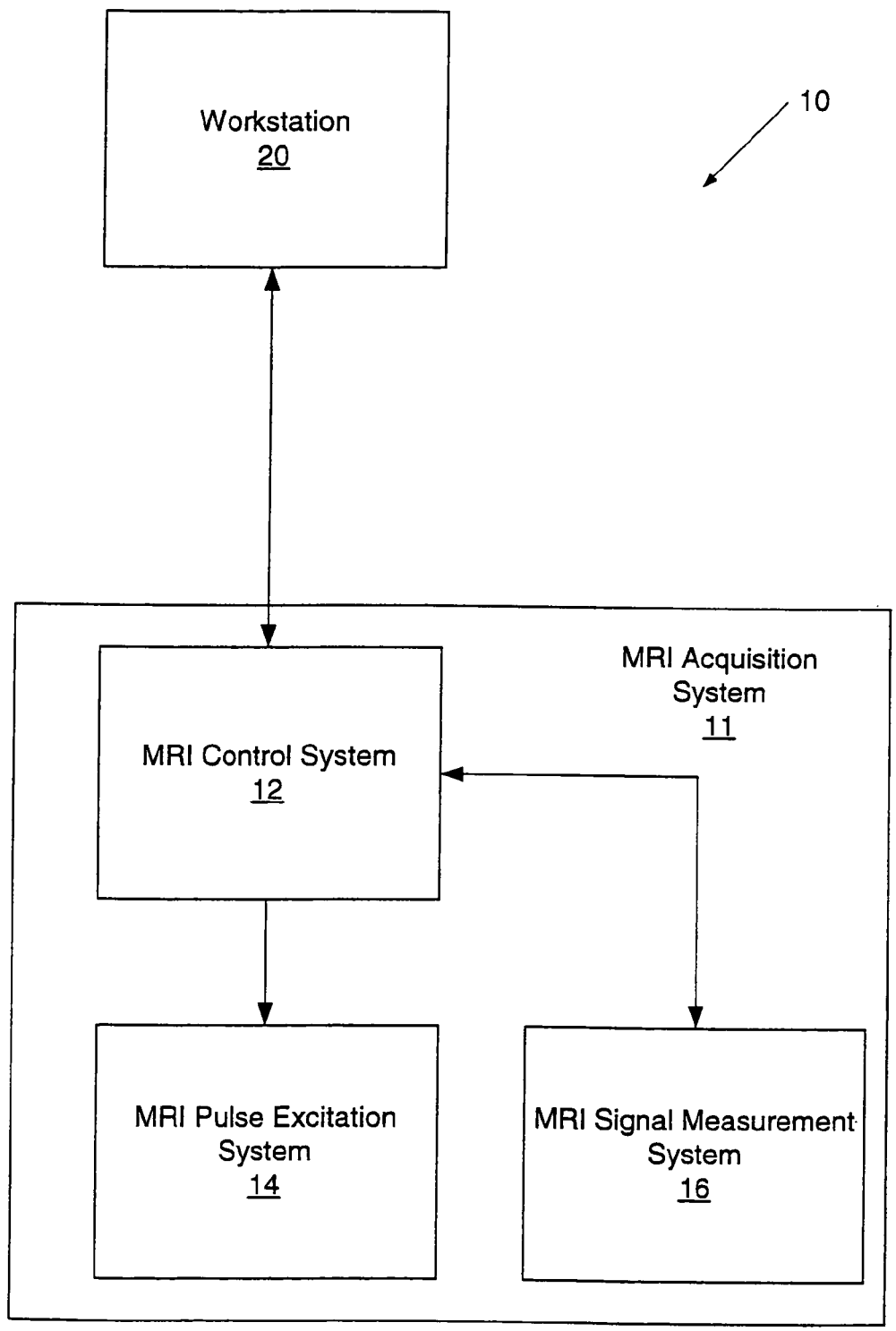
FIG. 1 is a block diagram of an MRI system according to embodiments of the present invention.

The present invention now will be described more fully hereinafter with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items. Broken lines illustrate optional features or operations unless specified otherwise. In the claims, the claimed methods are not limited to the order of any steps recited unless so stated thereat.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein. Well-known functions or constructions may not be described in detail for brevity and/or clarity.

As will be appreciated by one of skill in the art, the present invention may be embodied as methods, systems, or computer program products. Accordingly, the present invention may take the form of an entirely hardware embodiment, an entirely software embodiment or an embodiment combining software and hardware aspects all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on a user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider). Furthermore, the user's computer, the remote computer, or both, may be integrated into other systems, such as an MRI system and/or X-Ray Computed Tomography system.

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

MRI procedures are well established for identifying myocellular injury and LVEF in patients with ischemic cardiomyopathy secondary to coronary arteriosclerosis. Such procedures may identify localized cardiac injury. However, it is believed that such non-invasive imaging has not been utilized to identify global cardiac injury in patients with cardiomyopathy secondary to radiation and/or chemotherapy administration or other cardiac injuries.

Early detection of myocellular injury could offer an opportunity to adjust medication dosages and reduce and/or minimize the cardio-toxic effects associated with radiation and/or chemotherapy. In this manner, maximal doses of therapy could be administered to patients in the absence of myocellular injury and the desired effect of the therapy medications may be more fully realized. While embodiments of the present invention may be particularly useful in chemotherapy, such as doxorubicin therapy, embodiments of the present invention may also be utilized in other chemical therapies or regimens, and/or diagnostic environments where global cardiac injury is to be detected.

While embodiments of the present invention may be particularly useful in doxorubicin therapy, embodiments of the present invention may also be utilized in evaluating patients undergoing other chemical therapies and/or radiation therapy. Embodiments of the invention may be useful for evaluating global cardiac status in drug discovery programs, clinical trials and/or diagnostic environments using data from the detection of global cardiac injury.

Thus, it will be appreciated that although described herein primarily with respect to cardiotoxicity induced by chemotherapy and/or radiation, the evaluation techniques described herein can be used for other medical evaluations of cardiac injury and/or cardiotoxicity associated with and/or arising from other conditions, injuries or other toxic exposures. For example, embodiments of the present invention can evaluate cardiotoxicity associated with one or more of chemical or environmental toxin exposure (airborne, water, waste, and the like), poison (including chemical and/or insect, snake or other venoms), prescription or non-prescription drugs (such as those not associated with cancer), disease states, aging, viral, staff and bacterial infections, trauma and the like.

Embodiments of the present invention provide for detection of a change in tissue characteristics, such as may result from an injury utilizing a comparison of a global characteristic of a region of interest in an image of the region of interest. A global characteristic of a region of interest is a characteristic of the region of interest that is based on one or more characteristics of all or substantially all of the pixels/voxels of the region of interest. Thus, in certain embodiments of the present invention, the global characteristic may be substantially independent of the location of pixels within the region of interest. Examples of a global characteristic may include but are not limited to a statistical analysis of a characteristic of pixels/voxels in the region of interest such as average intensity, a histogram of intensity values or other statistical analysis. The use of a comparison of global characteristics of images may allow for detection of injury where the pattern of injury is random and/or is not detectable at the resolution of the images that are compared. Embodiments of the present invention may also use global characteristics, not only to detect injury to an area, but also to detect abnormal accumulation of materials that are not found in their normal ratios within native tissue.

Embodiments of the present invention may also be used with molecular imaging strategies: for example, directing the contrast with molecular recognition sites to areas of tissue and quantifying the presence of a target or molecular process. Thus, particular embodiments of the present invention may have application in detecting cancer, inflammation, infection, swelling or edema, scar tissue, etc. Also, embodiments of the present invention could be used to define metabolic pathways that are functioning within tissue in an organ system. Particular embodiments of the present invention provide for the detection of global cardiac injury utilizing non-invasive imaging before and/or after administration of a contrast agent and/or in connection to exposure to a toxin, such as, for example, a chemotherapeutic agent.

Non-invasive imaging techniques suitable for use in embodiments of the present invention include Magnetic Resonance Imaging (MRI), ultrasound, X-ray Computed Tomography (CT), single photon emission computed tomography (SPECT) and/or positron emission tomography (PET).

In some embodiments, comparisons may be made between a first or baseline image and a second image and the contrast of the image analyzed to detect the presence of global cardiac injury.

In some embodiments, at least one histogram of intensity of voxels of cardiac tissue from an image of a patient can be used to assess cardiotoxicity-induced cardiac injury. Typically, the image-based histogram data includes voxels of at least the left ventricle myocardium, where cardiac injury can be associated with reduced cardiac function, such as a decrement in LVEF that may result in a quality of life issue or a reduction in patient activity. Classification of the histogram data as being likely to result in cardiac injury can be based on norms of a population (or population segment, such as age, race, gender, etc.) or a statistical model of probability of cardiac injury based on histogram data, such as an undue decrement in LVEF (typically a decrease of greater than about 5%, more typically at least about 10% or greater, and/or a reduction below a threshold value of about 50% in a baseline image) associated with a high (and/or increased) value of intensity and/or one or more of a histogram shape, lineshape or voxel intensity distribution pattern.

In particular embodiments, a tail portion of the histogram of mean intensity voxels of an MRI or CT image of a left ventricle myocardium may include particularly predictive data that can be used to establish the probability of undesirable decrement in LVEF. One or more additional correlative factors may also be considered in a statistical correlation model, such as, but not limited to, left ventricle volume, mass, a patient's weight, age, gender, race, chemotherapeutic agent (s), chemotherapeutic dose and the like.

The terms "characterizing portion" or "characterizing predictive portion" means that the portion is statistically validated to be associated with cardiac injury and/or predictive of the presence of or a likelihood of developing a disease, injury or impairment. The term "tail portion" refers to a portion of a histogram of percentage (x-axis) versus intensity (y-axis) that is to the left of center or a peak (typically associated with higher intensity values) of the curve or shape. The tail portion may include a $2\sigma$, $3\sigma$, $4\sigma$, $5\sigma$ and/or $6\sigma$ portion of the intensity distribution of the curve associated with a voxel intensity histogram. Typically, the tail portion is a subset of the entire tail and may include only the portion representing a single sigma portion or combinations of one or more of a $1\sigma$, $2\sigma$, $3\sigma$, $4\sigma$ and/or $5\sigma$ portion of the histogram, for example, a $2\sigma$ and/or $3\sigma$ portion of the data or a $3\sigma$ and/or $4\sigma$, portion of the data. The tail portion can be another portion of the curve or shape if a different histogram construct is used. For example, if the intensity is on the x-axis and the percentage is on the y-axis, the characterizing portion of the curve may change using the same data.

The term "signature" means a recognizable (visually, optically or electronically recognizable) defined shape or pattern statistically correlated to be predictive of an actual or likelihood of developing a disease, injury or impairment.

The term "irreversible cardiac state" refers to a clinical change in heart function that is generally chronic (cannot self repair) that undesirably affects a patient's cardiac output or ability, whether in contractility, LVEF, pumping, rate or other quantitative measure.

The term "chemotherapy" and derivatives thereof refer to therapeutic medicaments, pharmaceuticals or other treatments used to treat a patient. Examples of chemotherapy agents include, but are not limited to, targeted antigens, antibodies, antineoplastics such as alkylating agents, nitrogen mustards, nitrosureas, antibiotics, hormonal antagonists or androgens, antiandrogens, antiestrogens, estrogen/nitrogen mixtures, estrogens, gonadotrooopin releasing hormones, immunomodulators, and other appropriate therapeutic agents. Examples of marker or expression-based evaluation of antigens/antibodies include those used in cancer evaluation and/or treatment. Examples of tumor-associated antigens of interest may include the CD-20 antigen (on B lymphocytes) for which treatment may include agents having antibodies to the CD-20 antigen and human epidermal growth factor (HER2) associated with some breast tumors. It is noted that HERCEPTIN® is currently approved for breast cancer treatment. It is contemplated that other biomaterials may also be suitable to as chemotherapeutic agents, including, but not limited to, mixed cultures containing tumor cells and blood-derived lymphocytes (which may be from the patient) to produce cytolytic T lymphocytes (CTL) (or CTL clones or autologous CTL), that lyse the autologous tumor cells (which may be used in connection with melanoma, renal, bladder, head and neck carcinomas, non-small lung cancer, and the like). Other potential antigens/antibodies of interest include MAGE-1, MAGE-3, BAGE, GAGE-1, and GAGE-3. See, e.g., UCL Christian de Duve Institute of Cellular Pathology, *Ludwig Institute For Cancer Research*, URL www.Icp.u-cl.ac.be/report95/licr95.html.

In some embodiments, a histogram or histograms taken at one or more points in time can be used to evaluate cardiotoxicity to determine a probability of increasing cardiac injury, before irreversible injury to the LVEF occurs. Such a probability of occurrence can be used to alter a planned chemotherapeutic dose, a change in the chemotherapeutic drug, and/or timing of administration of a chemotherapeutic dose.

As is known to those of skill in the art, the phrase "drawing a region of interest in air", does not literally mean "in air," but rather that the line or curve is drawn outside the body (and/or heart) in the image to obtain a corresponding background of noise data that can be used to adjust voxel intensity data.

As used herein, the term "image" refers to a spatial signal that may be evaluated to obtain a desired measure of signal intensity. The image can be visualized or displayed in 2-D what appear to be 3-D images, volume data representing features with different visual characteristics such as with differing intensity, opacity, color, texture and the like. Thus, as is well known in the art, the term "3-D" in relation to images does not require actual 3-D viewability (such as with 3-D glasses), but merely a 3-D appearance on a display.

As used herein, the term "global injury" refers to a change in tissue composition and/or function that is in a substantially randomly distributed pattern and/or in a pattern that is not detectable at the resolution of the images that are analyzed to detect the injury. Thus, for example, "global cardiac injury" may refer to cardiac injury and/or replacement of native myocardial tissue with fibrous tissue, such as scar tissue, that results in necrosis and/or fibrosis in a substantially randomly distributed pattern and/or in a pattern that is not detectable at the resolution of the images that are analyzed to detect the injury. Global cardiac injury that may be detected by intensity analysis according to embodiments of the present invention may include, for example, viral cardiomyopathy, alcoholic cardiomyopathy, postpartum cardiomyopathy and/or idiopathic dilated cardiomyopathy. A global injury may also include disproportionate amounts of other abnormalities such as edema (extra fluid), fibrosis (scar tissue), etc. Thus, embodiments of the present invention may provide for the detection of global abnormal tissue.

Contrast agents suitable for use in embodiments of the present invention may include paramagnetic lanthanide chelates and/or paramagnetic lanthanide linked to a macromolecule, such as gadolinium DPTA. Other examples of MR contrast for perfusion imaging include the application of susceptibility agents containing iron oxide or dysprosium that introduce local inhomogeneity into the magnetic field by causing large fluctuations in the magnetic moment between blood and intracellular compartments. Imaging after the introduction of other drugs that induce cardiomyopathy, such as cocaine and/or alcohol may also be performed. These fluctuations result in the shortening of T2-star of neighboring hydrogen nuclei leading to loss of signal intensity. It is contemplated that hyperpolarized contrast agents (such as hyperpolarized noble gas or carbon solutions) may also be used, particularly ones configured to be injected as solutions.

In particular embodiments of the present invention, the same contrast agent is utilized for each image.

Additionally, certain embodiments of the present invention may provide for contrast/intensity analysis without the administration of a contrast agent. For example, another example of perfusion imaging is the assessment of myocardial perfusion or injury without the administration of a contrast agent using a blood oxygen level dependent (BOLD) cardiac imaging via a T2-prepared true FISP, or 3D-T2-weighted sequence strategy. Other techniques use endogenous contrast including spin labeling and magnetization transfer contrast. Thus, in certain embodiments of the present invention, a global characteristic of a region of interest may be detected without the administration of a contrast agent.

An exemplary system 10 according to embodiments of the present invention is illustrated in FIG. 1. As seen in FIG. 1, an intensity analysis/MRI system 10 includes an MRI acquisition system 11 that may include an MRI control system circuit 12, an MRI pulse excitation system circuit 14 and an MRI signal measurement system circuit 16. The MRI control system circuit 12 controls operations of the MRI acquisition system 11 to obtain and provide MRI images during a cardiac cycle or portions thereof of a patient. The MRI control system circuit 12 may also assemble and transmit the acquired images to a workstation 20 or other such data processing system for further analysis and/or display. The workstation 20 may be in an MRI suite or may be remote from the MRI suite. The MRI pulse excitation system circuit 14 and the MRI signal measurement system circuit 16 are controlled to acquire MRI signals that may provide MRI images of the heart of a patient.

Conventional MRI systems, such as those provided by General Electric Medical Systems, Siemens, Philips, Varian, Bruker, Marconi, Hitachi and Toshiba may be utilized to provide the desired MRI image frames collected (typically after administration of a contrast agent) and/or with a suitable pulse acquisition technique. The MRI systems can be any suitable magnetic field strength, such as, for example, about 1.5 T, and may be higher field systems of between about 2.0 T-10.0 T.

While an exemplary intensity analysis/MRI system is illustrated in FIG. 1 and described herein with a particular division of functions and/or operations, as will be appreciated by those of skill in the art, other divisions of functions and/or operations may be utilized while still benefiting from the teachings of the present invention. For example, the MRI control system circuit 12 could be combined with either the MRI pulse excitation system circuit 14 or the MRI signal measurement system circuit 16. Thus, the present invention should not be construed as limited to a particular architecture or division of MRI functions/operations but is intended to cover any architecture or division of functions/operations capable of carrying out the operations described herein.

Figure 2:
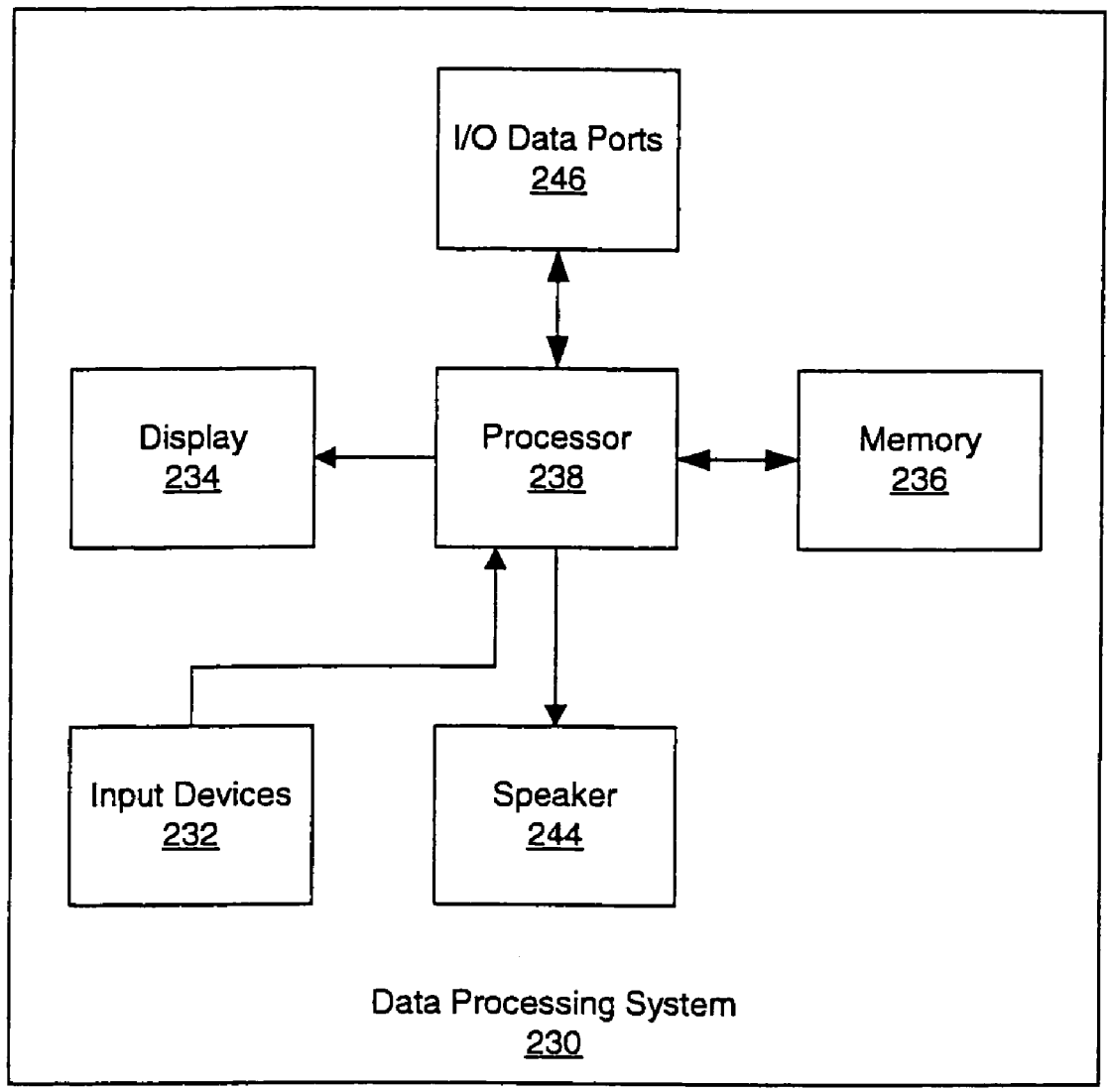
FIG. 2 is a block diagram of a data processing system according to embodiments of the present invention.

FIG. 2 illustrates an exemplary embodiment of a data processing system 230 suitable for providing a workstation 20 and/or MRI control system circuit 12 in accordance with embodiments of the present invention. The data processing system 230 typically includes input device(s) 232 such as a keyboard or keypad, a display 234, and a memory 236 that communicate with a processor 238. The data processing system 230 may further include a speaker 244, and an I/O data port(s) 246 that also communicate with the processor 238. The I/O data ports 246 can be used to transfer information between the data processing system 230 and another computer system or a network. These components may be conventional components such as those used in many conventional data processing systems that may be configured to operate as described herein.

Figure 3:
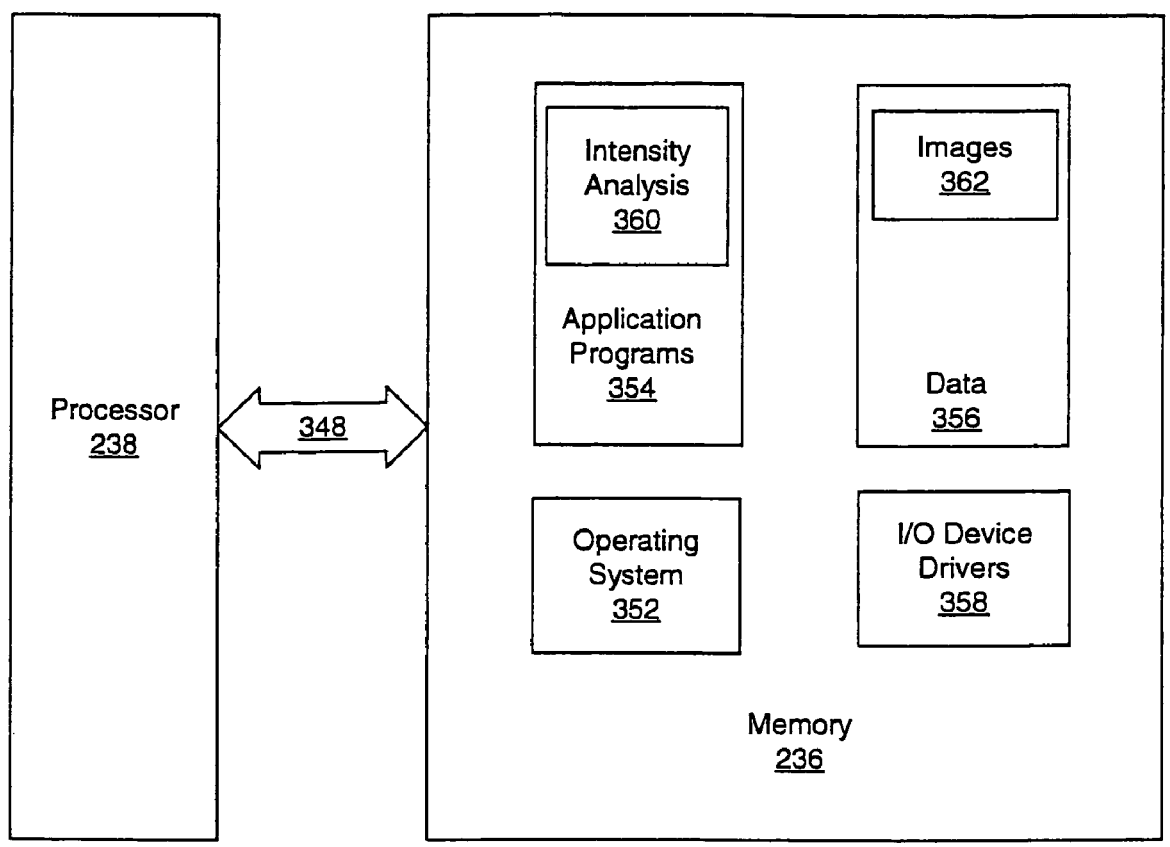
FIG. 3 is a block diagram of a data processing system according to embodiments of the present invention.

FIG. 3 is a block diagram of embodiments of data processing systems that illustrates systems, methods, and computer program products in accordance with embodiments of the present invention. The processor 238 communicates with the memory 236 via an address/data bus 348. The processor 238 can be any commercially available or custom microprocessor. The memory 236 is representative of the overall hierarchy of memory devices containing the software and data used to implement the functionality of the data processing system 230. The memory 236 can include, but is not limited to, the following types of devices: cache, ROM, PROM, EPROM, EEPROM, flash memory, SRAM, and DRAM.

As shown in FIG. 3, the memory 236 may include several categories of software and/or data used in the data processing system 230: the operating system 352; the application programs 354; the input/output (I/O) device drivers 358; and the data 356. As will be appreciated by those of skill in the art, the operating system 352 may be any operating system suitable for use with a data processing system, such as OS/2, AIX or System390 from International Business Machines Corporation, Armonk, N.Y., Windows95, Windows98, Windows2000, WindowsNT or WindowsXP from Microsoft Corporation, Redmond, Wash., Unix or Linux. The operating systems may be configured to support a TCP/IP-based or other such network communication protocol connection. The I/O device drivers 358 typically include software routines accessed through the operating system 352 by the application programs 354 to communicate with devices such as the I/O data port(s) 246 and certain memory 236 components. The application programs 354 are illustrative of the programs that implement the various features of the data processing system 230 and preferably include at least one application that supports operations according to embodiments of the present invention. Finally, the data 356 represents the static and dynamic data used by the application programs 354, the operating system 352, the I/O device drivers 358, and other software programs that may reside in the memory 236.

As is further seen in FIG. 3, the application programs 354 may include an intensity analysis application 360. The intensity analysis application 360 may carry out the operations described herein for evaluating images to detect changes in intensity that may be associated with global cardiac injury. The data portion 356 of memory 236, as shown in the embodiments of FIG. 3, may include image data 362, such as MRI image data that includes first and second images of tissue of a region of interest for comparison.

While the present invention is illustrated, for example, with reference to the intensity analysis application 360 being an application program in FIG. 3, as will be appreciated by those of skill in the art, other configurations may also be utilized while still benefiting from the teachings of the present invention. For example, the intensity analysis application 360 may also be incorporated into the operating system 352, the I/O device drivers 358 or other such logical division of the data processing system 230. Thus, the present invention should not be construed as limited to the configuration of FIG. 3 but is intended to encompass any configuration capable of carrying out the operations described herein.

Figure 4A:
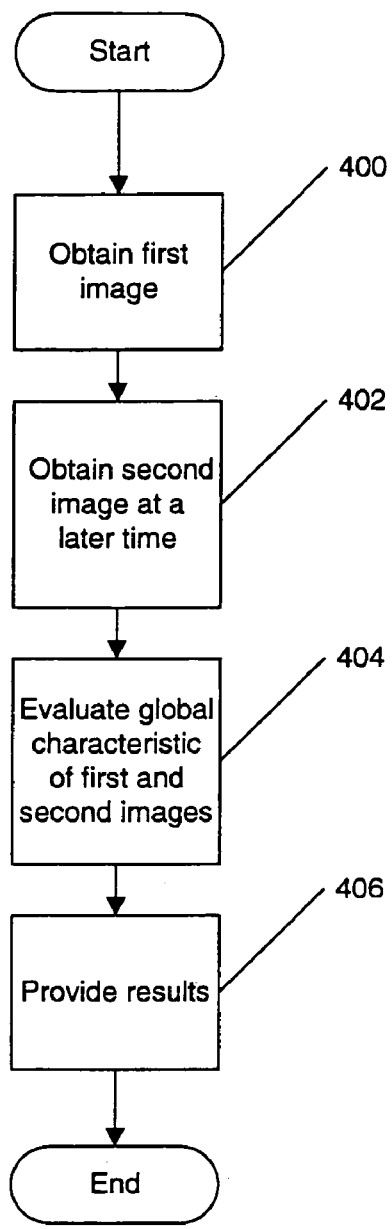
FIGS. 4A and 4B are flow charts illustrating operations according to certain embodiments of the present invention.

FIG. 4A illustrates operations according to particular embodiments of the present invention. As seen in FIG. 4A, a first image of a region of interest of tissue of a patient is obtained (block 400). An image may be obtained, for example, by acquisition of the image from an imaging system, such as the imaging systems discussed above, and/or by obtaining the image from a database, file or other storage of the image data. For example, a patient's images may be maintained in a historical database for subsequent recall as a first image for comparison. The region of interest of tissue in a patient that is imaged may, for example, include heart, blood, muscle, brain, nerve, skeletal, skeletal muscle, liver, kidney, lung, pancreatic, endocrine, gastrointestinal and/or genitourinary tissue. In particular embodiments of the present invention, the tissue may be human tissue. In other embodiments, the tissue may be animal tissue.

As is further illustrated in FIG. 4A, a second image of the tissue in the region of interest for comparison to the first image is obtained after a period of time, such as hours, days, weeks, months or even years (block 402). The second image for comparison reflects any change in the characteristics of the tissue in the region of interest. The second, comparison image may be acquired and registered (taken at the same slice locations) with the corresponding first image. The second image may also be obtained as described above with reference to the first image. Thus, for example, comparison images may be historical images as well as recently acquired images.

The first image and the second image are evaluated to determine one or more global characteristics of the images (block 404). The global characteristic of the images may, for example, be an average intensity of pixels/voxels in the region of interest. The global characteristic could also be a statistical analysis of the pixels/voxels in the region of interest. For example, the standard deviation, mean value or other statistical analysis of the pixels/voxels in the region of interest could be determined. Also, a histogram of a characteristic of the pixels/voxels in the region of interest could be provided as a global characteristic. The characteristic of the pixels/voxels that is evaluated to provide the global characteristic may include intensity, color, saturation and/or other characteristics of individual pixels/voxels as well as relative characteristics of multiple pixels/voxels, such as contrast ratios or the like.

The results of this evaluation are provided to a user or may be provided for further analysis (block 406). For example, a comparison of the first image and the second image may be performed and a difference in average intensity may be provided as results to a user. Furthermore, a histogram of the characteristic and/or differences in the characteristic between the baseline and comparison images may be determined and provided as a result. Additionally, the histogram could be pattern matched to a library of histogram profiles that are characteristic of particular injuries, diseases and/or conditions. The results of the determination may, for example, be provided as part of a graphic user interface The results of the evaluation of the global characteristic of the image of the tissue in the region of interest may be utilized in the detection, perhaps the early detection, of change in tissue characteristics such as may result, for example, from injury to the tissue or other conditions as discussed above. Such a global characteristic evaluation may be suitable in detecting tissue characteristics that result in a random pattern of different tissue characteristics in the region of interest or that are imaged at a resolution where a pattern of the tissue characteristic cannot be detected.

Figure 4B:
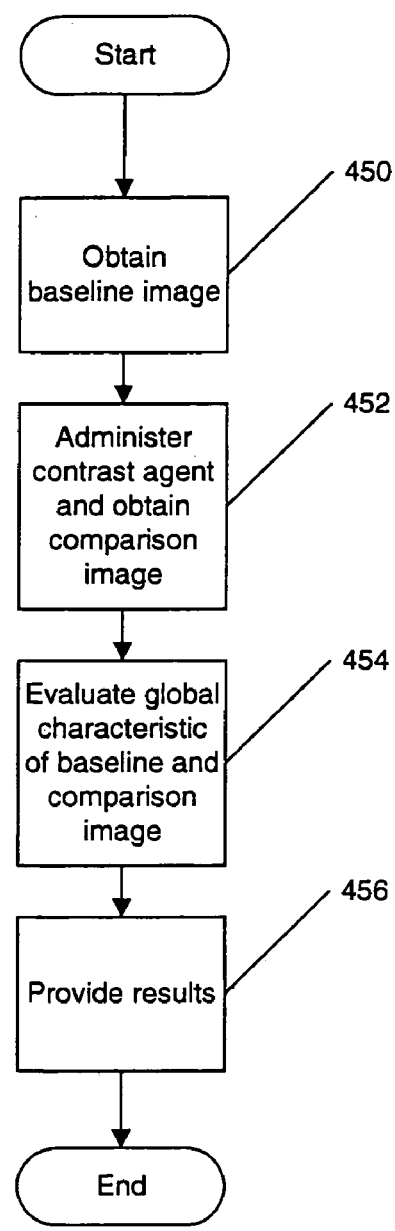

FIG. 4B illustrates operations according to particular embodiments of the present invention utilizing administration of a contrast agent. As seen in FIG. 4B, a baseline image of a region of interest of tissue of a patient is obtained (block 450). An image may be obtained, for example, by acquisition of the image from an imaging system, such as the MRI system illustrated in FIG. 1, and/or by obtaining the image from a database, file or other storage of the image data. For example, a patient's images may be maintained in a historical database for subsequent recall as a baseline image for comparison. The baseline image may be an image taken without administration of a contrast agent, after administration of a contrast agent and/or a period of time, such as twenty minutes, after administration of the contrast agent. The region of interest of tissue in a patient that is imaged may, for example, include heart, blood, muscle, brain, nerve, skeletal, skeletal muscle, liver, kidney, lung, pancreatic, endocrine, gastrointestinal and/or genitourinary tissue. In particular embodiments of the present invention, the tissue may be human tissue. In other embodiments, the tissue may be animal tissue.

As is further illustrated in FIG. 4B, an image of the tissue in the region of interest for comparison to the baseline image is obtained after administration of a contrast agent (block 452). The image for comparison reflects the effect of the contrast agent on the tissue in the region of interest. In particular embodiments of the present invention, the image may be a myocardial delayed enhancement (MDE) image. The comparison image may be acquired and registered (taken at the same slice locations) with the corresponding baseline image. The comparison image may also be obtained as described above with reference to the baseline image. Thus, for example, comparison images may be historical images as well as recently acquired images.

The baseline image and the comparison image are evaluated to determine one or more global characteristics of the images (block 454). The global characteristic of the images may, for example, be an average intensity of pixels/voxels in the region of interest. The global characteristic could also be a statistical analysis of the pixels/voxels in the region of interest.

For example, the global characteristic can be the standard deviation, comparison of mean, average characteristics, histogram shape, such as skew and kurtosis, or distribution of intensities within the histogram, other moment of analysis, or other statistical analysis of the pixels/voxels in the region of interest. Also, a histogram of a characteristic of the pixels/voxels in the region of interest could be provided as a global characteristic. The characteristic of the pixels/voxels that is evaluated to provide the global characteristic may include intensity, color, saturation and/or other characteristics of individual pixels/voxels as well as relative characteristics of multiple pixels/voxels, such as contrast ratios or the like.

In some particular embodiments, one of equations (1)-(3) may be used to evaluate voxel data. The standard deviation (spread of the distribution) may be defined by mathematical equation (1).

$$s = \sqrt{\frac{1}{n-1} \sum_{i=1}^{n} (x_i - \overline{x})^2} \quad \text{Equation 1}$$

where "n" is the number of voxels measured for one individual, $x_i$ is the individual intensity of voxel i, and $\overline{x}$ is the mean of the voxels.

The skewness of the distribution, which measures the symmetry of the distribution can be defined by equation (2).

$$\frac{\sum_{i=1}^{n} \frac{(x_i - \overline{x})^3}{s^3}}{n} \quad \text{Equation 2}$$

where n, $x_i$ and $\overline{x}$ are as defined above for equation (1) and s is the standard deviation of the distribution of voxels as defined above.

The kurtosis of distribution is a measure that describes the "tails of the distribution" and may also be known as the "peakedness" of a distribution. The kurtosis can be defined by equation (3).

$$\frac{\sum_{i=1}^{n} \frac{(x_i - \overline{x})^4}{s^4}}{n} - 3 \quad \text{Equation 3}$$

where n, s, $x_i$ and $\overline{x}$ are as defined above. If data were normally distributed the skewness and kurtosis, as defined above, both would be zero (which is not the typical situation for cardiac toxicity or injury).

The results of this evaluation are provided to a user or may be provided for further analysis (block 456). For example, a comparison of the baseline image and the comparison image may be performed and a difference in average intensity may be provided as results to a user. Furthermore, a histogram of the characteristic and/or differences in the characteristic between the baseline and comparison images may be determined and provided as a result. Additionally, the histogram could be pattern matched to a library of histogram profiles that are characteristic of particular injuries, diseases and/or conditions. The results of the determination may, for example, be provided as part of a graphic user interface The results of the evaluation of the global characteristic of the image of the tissue in the region of interest may be utilized in the detection, perhaps the early detection, of injury to the tissue. Such detection may be provided for injuries that result in a different concentration of contrast agent being present in injured versus healthy tissue. Such a global characteristic evaluation may be suitable in detecting injuries that result in a random pattern of injured tissue in the region of interest or that are imaged at a resolution where a pattern of the injured tissue cannot be detected. Thus, for example, with a 1.5 Tesla MRI imaging system, a typical myocardial infarct would not be considered a global image and the detection and location of increased intensity in an image in the location of the infarct would not be considered a random pattern of injured tissue or a pattern of injured tissue that could not be detected at the resolution of the MRI imaging system.

Figure 5:
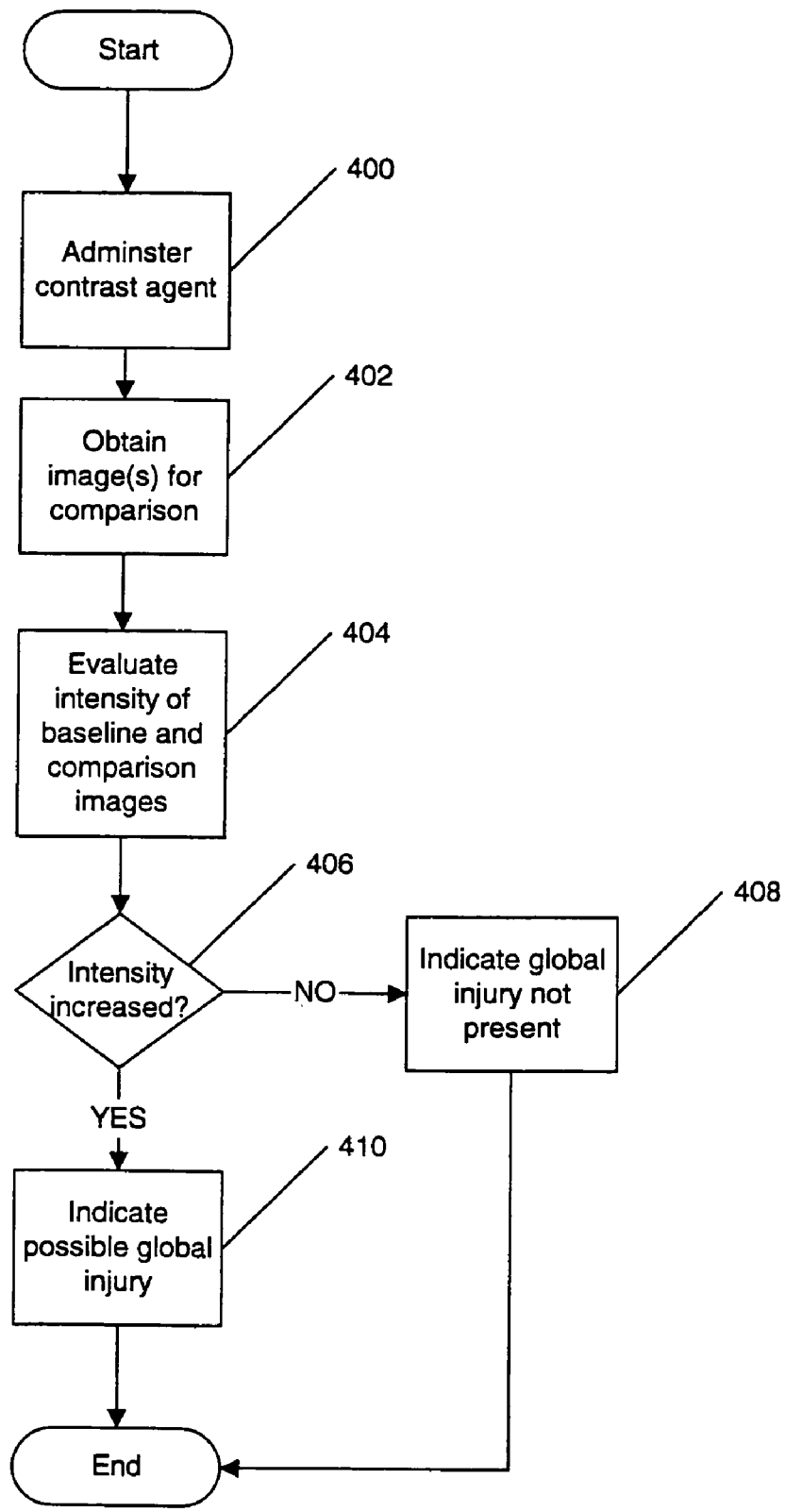
FIG. 5 is a flow chart illustrating operations according to certain embodiments of the present invention.

FIG. 5 illustrates operations according to particular embodiments of the present invention. As seen in FIG. 5, a contrast agent is administered to a patient (block 400) and an image of at least a portion of the patient's heart is acquired (block 402). In particular embodiments of the present invention, the acquired perfusion image may be a myocardial delayed enhancement (MDE) image. In MDE, after about 20 minutes after a contrast agent, such as gadolinium DPTA, is administered, ordinarily some of it has leaked into necrotic (dead) tissue and will appear bright (hence, delayed enhancement). These images may be acquired and registered (taken at the same slice locations and/or processed to align at the same locations) with the corresponding baseline perfusion images.

The acquired image is evaluated and the intensity of the image is compared to a baseline image (block 404). The baseline image is an image of the patient's heart and may be a previously acquired image that was also acquired after administration of a contrast agent. The baseline image may have been acquired prior to administration of a treatment regimen or may be an image acquired at an earlier evaluation. The comparison of images may be a comparison of average intensity and/or mean intensity of the images as discussed in more detail below. If the intensity of the image has not increased in comparison to the baseline image (block 406), then an indication that a global cardiac injury is not present may be provided (block 408). If the intensity of the image has increased in comparison to the baseline image (block 406), then an indication that a global cardiac injury may be present may be provided (block 410).

In still further embodiments of the present invention, the evaluation of global image characteristics, such as the intensity of the cardiac images, may be performed automatically or partially automatically utilizing image processing techniques. An automatic comparison may, for example, also include registration of the differing images to each other. Such a registration may be provided utilizing conventional pattern recognition and/or alignment techniques such that corresponding pixels of the images or portions of the images are each associated with approximately the same physical location within the patient.

In particular embodiments, registration may be across the entire left ventricle myocardium using a plurality of slices, such as at least about three, typically at least about eight, and more typically about 10, short axis slices per patient. Co-registration may be calculated as the union of left ventricle voxel locations which may be carried out to provide at least about a 95% overlap of regions between images.

In particular embodiments of the present invention, a patient may be taken to the MRI suite where he/she will be placed supine on the MRI table and ECG leads and respiratory gating bellows applied. MRI scans may be performed on, for example, a 1.5 Tesla GE CV$_i$ scanner with a phased array surface coil applied around the chest to optimize signal to noise ratio or on another MRI scanner. Images may be acquired using a fast gradient echo technique, with the repetition time (TR) and echo time (TE) based on the R-R interval of the subject. Multislice coronal, gradient echo sequences may be used to obtain scout images of the chest and locate the left ventricle. Subjects may be injected intravenously with a gadolinium contrast agent (0.2 mmole/kg Gadoteridol (Prohance, Bracco Diagnostics, Princeton, N.J.)). The time of this injection may be recorded.

After locating the left ventricle, a series of steady state free precession, short axis views can be acquired perpendicular to the left ventricle covering from the base to the apex. Imaging parameters can be, for example, 32 cm field of view, 35 degree flip angle, 8 mm slice thickness, 2 mm inter-slice space, and a 256×128 matrix. The scans may have a temporal resolution of about 40 msec to identify end systole for determinations of LV volumes, EF (ejection fraction) and mass using known protocols. See, Natori et al., *Cardiac MR Imaging in MESA: Protocol and Normal Values*, AM J Roentgenol (In Press) (describing a multi-center cohort study such as the Mutli-Ethic Study of Atherosclerosis with greater than 6000 subjects). For example, to measure LV volumes, a series of LV short axis views spanning the base to the apex of the heart can be acquired. The volume is determined by summing the endocardial area within each slice multiplied by the slice thickness. Endocardial area in each segment can be calculated at end-diastole and end systole. This technique is known as Simpson's rule technique and can calculate volumes without using formulas with assumptions about LV shape. Left ventricular ejection fraction can be calculated using the relationship: (end-diastolic volume-end-systolic volume)/end-diastolic volume. See Semelka et al: *Interstudy reproducibility of dimensional and functional measurements between cine magnetic resonance studies in the morphology abnormal left ventricle*, Am. Heart J. 119:1367-1373 (1990).

About twenty minutes from the time of the contrast injection, at least three short axis views in the same slice positions as the LV volume determinations, such as (basal, middle, and apical) delayed enhancement images, may be acquired using a fast gradient echo preceded by a nonselective saturation pulse. Landmarks for these acquisitions may be measured from the coronary sinus within the atrio-ventricular groove extending horizontally across the mitral valve annulus. These images may be acquired using a 38 cm field of view, 24 views per segment, 8 mm slice thickness (2 mm gap), 2 NEX, 256×256 imaging matrix, and a 0.75 rectangular field of view. The inversion time (TI) for the delayed enhancement images may be adjusted 140 to 160 msec to provide a uniform dark background. Additionally, in these three short axis slice positions, a fast-gradient-recalled echo pulse sequence may be used with phase-encode ordering. These images may be subjected to phase-sensitive reconstruction that reduces the variation in apparent contrast intensity that is observed in the magnitude images as TI is changed. In addition, the phase-sensitive reconstruction may decrease the sensitivity to changes in tissue $T_1$ with increasing delay from the gadolinium contrast injection.

Upon completion of the image acquisition, the locations, measurements, and representative images may be transferred electronically to a database. This information may be available to the MRI technologist via a PC workstation at the time of each scan and facilitate the relocation of slice positions (registration) on subsequent studies.

Figure 12:
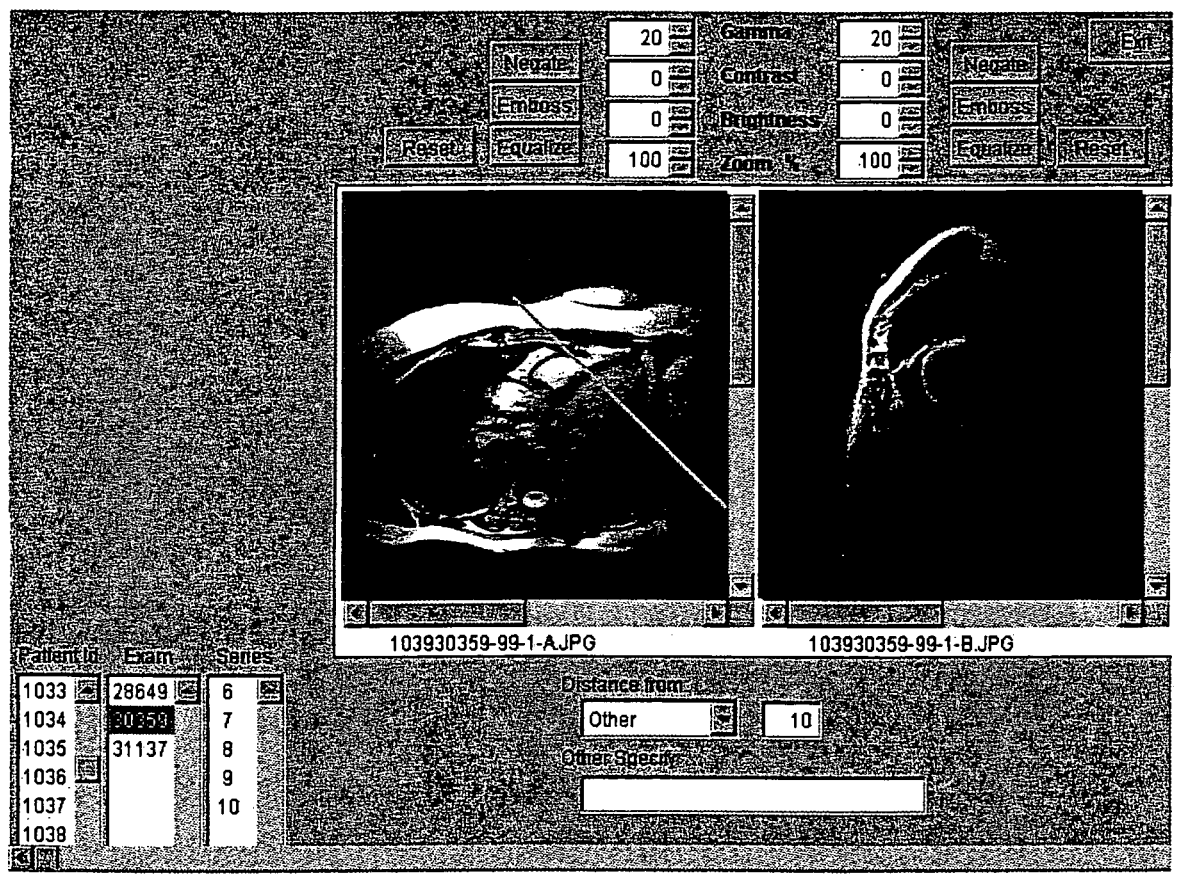
FIG. 12 is a screen capture of image planning software for reproducing slice positions.

FIG. 12 illustrates a screen capture of software for planning image slices. Such software may provide electronic copies of image planning slices and positioning coordinates that are saved for retrieval during subsequent visits in a study. This has the effect of improving the ability of the MRI technologist to reproduce slice positions from the previous visits. In the example of FIG. 12, a long-axis view of the heart with a resultant delayed enhancement short axis view is shown.

On the delayed enhancement acquisitions, regions of interest (ROIs) encompassing the LV myocardium on all of the multi-slice acquisitions may be determined. High signal intensities associated with the blood pool within the LV cavity may be avoided. The signal intensity and location (x, y, and z coordinates) of each (or selected) voxel within the ROI's may be recorded from both baseline and delayed enhancement images. Values may also be derived from subtracting the mean intensity for a separate ROI, for example, without contrast agent, from the intensities by using a separate ROI within the air/space outside of the body. The ROI's may be utilized as discussed below in the Examples in determining a change in intensity between two images. The region of interest can be a three-dimensional region having an associated thickness.

In some embodiments, a slice position between first and second acquisitions (or more) can be aligned using physician interactive tools that can allow the physician to draw freehand or with software-guidance (i.e, GUI tools such as adjustable size/shape curves), the endo- and epi-cardial boundaries of the LV myocardium and can also allow a physician to define a region of interest for the background noise in the air as discussed above. The defined LV boundaries can help avoid high signal intensity voxels located beyond the LV myocardium. This background ROI can be automatically sized to have the same area (hence the same number of voxels) as the annular LV ROI. This may facilitate proper scaling for the subtraction of the air histogram from the LV histogram in the noise removal process. Histograms of the voxel intensities in the LV or air regions, as well as a difference histogram, can be plotted using automated software algorithms with customization options. A 3-D image of the heart illustrating the different voxel intensities may be generated; such an image differs from conventional CMR images in that voxel intensities are quantified (relatively or absolutely) and visually indicated on the image with similar intensities having similar greyscale or color (such as with different and graduated shades of color for different voxel intensities) to emphasize the distribution on injured or dead cells over the heart and/or target compartments of the heart. Thus, the heart can be illustrated "lit-up" with visually accentuated regions of impaired or dead cells for ease of viewability and reference for a clinician.

In some embodiments, other known noise or background removal strategies can be employed, such as, for example, Wiener and Kalman filtering, that can consider the location of noise voxels removed from the image. See Gonzalez et al., *Digital Image Processing*, Addison-Wesley Pub. Co., p. 279 (1992).

Figure 13:
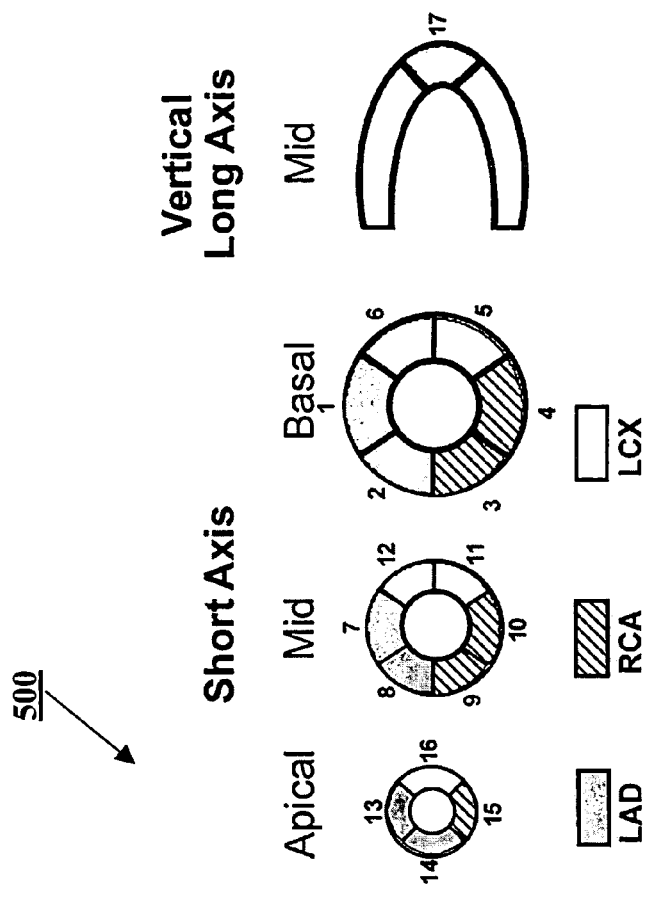
FIG. 13 is a schematic illustration of a standardized compartmental heart model.
Figure 13:
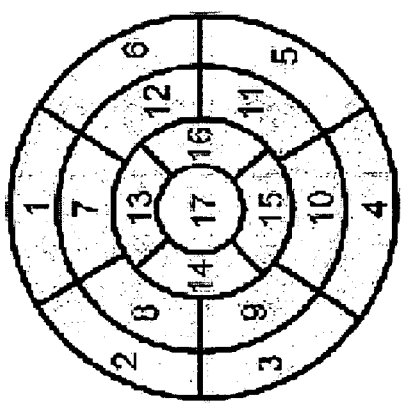

In some embodiments, a standardized model of the heart 500 can be visually generated with the voxel intensity data such as shown in FIG. 13. The model shown in FIG. 13 is a 17-segment (compartment) model of the heart that can visually illustrate cardiac status to a clinician. This model corresponds to the model developed by the American Heart Association and the American College of Cardiology to standardize reporting of radionuclide scintigraphy, echocardiography, Computed Tomography and MRI data related to LV myocardial function, perfusion and injury. As shown, regional blood flow to the compartments or segments in the model can be ascribed to the left anterior descending anterior (LAD), right (RCA) and circumflex (LCX) coronary arteries. See Cerqueira et al., *Standardized Myocardial segmentation and nomenclature for tomographic imaging of the heart: A statement for healthcare professionals from the cardiac imaging committee of the council on clinical cardiology of the American Heart Association*, Circulation: 105: 539-542 (2002). The model can be displayed on the physician workstation (or electronically stored in memory at a suitable local or remote site) as a color-coded graphic display in any suitable format, such as, but not limited to, GIF, TIFF, JPEG or BMP. The model 500 can be configured to display adjacent one or more histograms of different slices of intensity data at a physician workstation. The 17 compartments are listed below.

---

1. basal anterior
2. basal anteroseptal
3. basal inferoseptal
4. basal inferior
5. basal inferolateral
6. basal anterolateral
7. mid anterior
8. mid anteroseptal
9. mid inferoseptal
10. mid inferior
11. mid inferolateral
12. mid anterolateral
13. apical anterior
14. apical septal
15. apical inferior -continued 16. apical lateral
17. apex

---

It is contemplated that employing the standardized model using CMR intensity data alone or with data from other techniques can provide additional information in the process of myocellular injury in patients, for example, patients receiving radiation and/or chemotherapy. Further, a determination of the relationship between regional myocellular injury and global LVEF change may be established. For example, in ischemic cardiomyopathy, injury to the apical LV segments is associated with reduced exercise capacity and an increased incidence of future myocardial infarction or death when compared to injury in basal myocardial segments.

Figure 14:
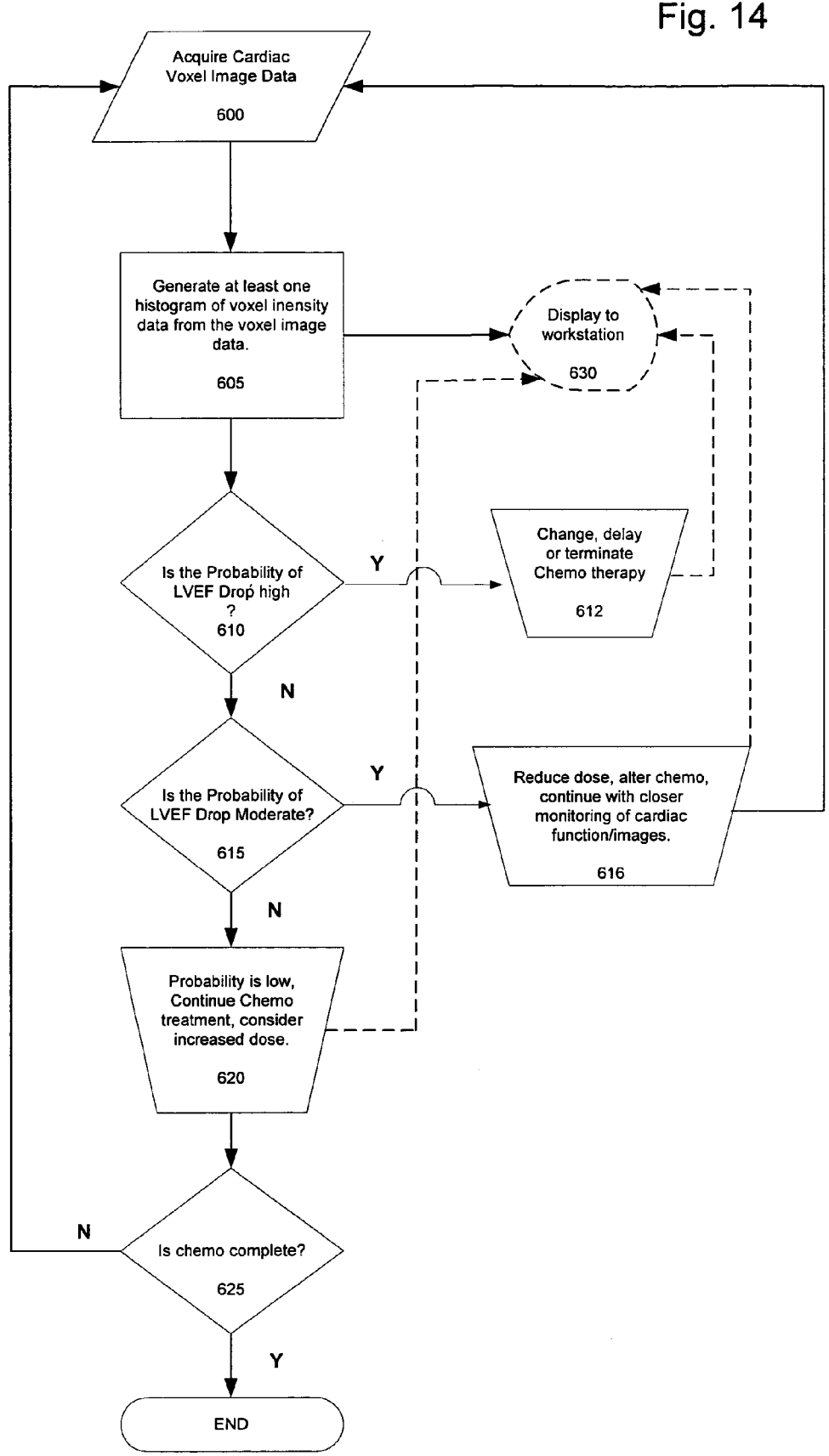
FIG. 14 is a flow chart of operations that can be carried out according to embodiments of the present invention.

FIG. 14 illustrates a non-invasive monitoring tool (which can be compared to a non-invasive biopsy) that can be used during a course of treatment of an oncology patient to monitor cardiotoxicity. As shown, cardiac image voxel data can be acquired (block 600). The image typically includes an image of at least the left ventricle myocardium. At least one histogram of the image data can be generated from the voxel image data (block 605). The histogram can be of intensity (average, mean or other measure of intensity) voxel distribution in regions of interest across the volume of the left ventricle myocardium including one or more of the apex, base or mid regions. In particular embodiments, a mean intensity histogram can be generated. An algorithm can electronically analyze the histogram data and determine if the probability of LVEF drop is high (block 610). In some embodiments, the algorithm can electronically evaluate a tail portion of the histogram to determine the probability of a future undesirable drop in LVEF, if chemotherapy is continued. The algorithm can include pattern recognition or electronic correlation analysis software that can analyze one or more of a line shape, distribution pattern, and/or histogram shape (particularly of the tail portion of the histogram). If the probability is high, then the clinician can be notified to determine if the chemotherapy should be changed (block 612). A clinician (such as an oncologist or other physician) may then decide how to proceed before the next planned active chemo delivery, such as, for example, decrease the dose, change the drug or drug combo, delay the next treatment, prescribe a medicament to help alleviate the condition, or terminate the chemo altogether (perhaps initiating an alternative treatment, such as a radiation treatment). If the probability is determined to be moderate (block 615), then a clinician can determine whether to decrease the dose, alter the chemotherapy regimen, change the chemotherapy drug(s), or increase the monitoring frequency (block 616). If the probability is considered low (block 620), the chemotherapy can continue as planned, and/or a physician may even increase the dose as needed. If the next round of chemotherapy is not the last, the sequence of operations described above can be repeated. The sequence of operations may be carried out at 1 month, 2 months and 4 months into chemotherapy and may include a baseline evaluation prior to initiation of chemotherapy.

As shown, optionally, the histogram results can be provided to a display associated with a clinician's workstation and/or each of the probability calculations and/or results can be provided to the display as well (block 630). The relative or absolute "high", "moderate" and "low" probabilities can be defined in any appropriate absolute or relative manner. However, "high" probability typically means that the likelihood that an undesired drop in LVEF (it is contemplated that the undesired drop may correlate to at least about 5%, and typically (clinically) about 10% or more) will occur if the planned chemotherapy continues is about 75% or greater. The term "moderate" means between about 25%-74% probability that the LVEF drop will occur, and the term "low" means that there is less than about a 25% chance that the LVEF drop will occur.

The chemotherapy monitoring tool can be configured to consider factors other than the histogram to determine risk: for example, the type of radiation and/or chemotherapy protocol or regime, the number of doses received at the time of the reading, previous cardiac history, and the like. For example, about 85% of patients experiencing toxicity will do so after receipt of approximately 100 mg/m$^2$ of doxorubicin (usually at T=1 month). Thus an evaluation before that time that indicates a moderate risk may be elevated to a probable risk for future events. That is, if a patient presents with a "moderate" probability risk at baseline, after a first dose, and/or when associated with a drug or drug combination known to induce more severe cardiotoxicity reaction, then this data may be considered to make the patient at high risk for the planned chemo treatment.

Because the monitoring is non-invasive, a clinician can request daily, weekly, monthly, or at other desired schedules of review and may even use the monitoring data to help time the spacing and/or date of the chemotherapy delivery itself and/or to titrate a dose for that patient.

The operations can be carried out to generate a report of probabilities of cardiotoxicity response. The report can be an electronic and/or paper report, and may be generated in substantially real-time or shortly after acquisition of the image data. A first baseline image can be obtained prior to initiation of a chemotherapy regime. Alternatively, one or more monitoring images can be obtained at various times during the course of chemotherapy. In some embodiments, a respective image can be obtained and the LVEF drop predictive analysis performed before each round of chemotherapy, particularly each later round of chemotherapy. Alternatively, the analysis can be carried out after (or even during) a chemotherapy administration. The monitoring process can generate an alert to notify a physician if a probability is high or moderate, before irreversible injury associated with an undesired drop in LVEF actually occurs. This alert of probabilities of an undesirable response can allow a clinician to alter the planned therapy before actual irreversible LVEF injury occurs.

While embodiments of the present invention have been described above with respect to particular views, regions, areas and/or slices of the heart, other views, regions, areas and/or slices of the heart may also be utilized. Furthermore, fewer or greater than three slices may be utilized. Different numbers of slices may be used for different patients. For example, three slices may be appropriate to sufficiently evaluate a heart of a young child, while about 20 may be required for a heart of a large person, with an average number of slices being about 10.

Additionally, the images may be taken along the long or short axis of the heart. Accordingly, certain embodiments of the present invention should not be construed as limited to the particular views of the heart but may include any view and/or number of views of the heart that allow for intensity analysis to detect global cardiac injury.

Typically, a first baseline image will be obtained prior to or early in treatment or as an initial reference point in diagnosis of change in cardiac condition. Subsequent images for comparison may be taken daily, weekly or at other fixed or variable interval(s) or prior to or after a planned treatment, such as a cytotoxic treatment.

It is noted that for some embodiments including voxel data from the left ventricle is of particular interest in assessing cardiac injury and/or cardiotoxicity has been described above. However voxel data from other regions of the heart, including for example, the right ventricle and/or the base or tip may be employed. Combinations of two or more spaced apart regions of interest in different heart locations may also be used to evaluate cardiac injury and/or risk of injury. The region(s) so selected, when having impaired or dead cells identified by image voxel data, can be associated with reduced cardiac function and/or a present or future increased risk of cardiac dysfunction or even cardiac-induced morbidity.

It is contemplated that voxel data can help identify impaired cells as well as necrotic tissue. That is, in some embodiments, voxel data can be used to visualize or detect cell injury, such as that associated with inflammation or accumulation of water around cells in the heart, which can inhibit contractility and impair cardiac function. The impaired cell data can also be used to predict future irreversible cardiac injury or a more severe drop in function or contractility, oxygenation, valve function and the like.

In some embodiments, a clustering of impaired or dead cells in one or more volumetric regions of interest can be used to indicate present cardiac injury and/or predict future cardiac injury associated with undesirable cardiac dysfunction. The clustering-effect may have more relevance for the non "super hot" voxels (super-hot refers to the highest intensity voxels), such as, for example, where clusters of relatively mid-intensity voxels appear in certain compartments of the heart. See, e.g., the arrows that point to exemplary range voxels in FIG. 16.

Some embodiments of the invention may be used to evaluate how drugs affect cardiac tissue for pharmacological studies, such as, for example, clinical trials and/or drug discovery or even safety assessments of already regulatory (FDA) approved drugs.

It will be appreciated that although described above primarily with respect to cardiotoxicity induced by chemotherapy, the evaluation techniques described herein can be used for other medical evaluations of cardiac injury and/or cardiotoxicity due to other conditions, injuries or other toxic exposures. For example, embodiments of the present invention can evaluate cardiotoxicity associated with one or more of environmental toxin exposure (airborne, water, waste, and the like), poison (including insect, snake or other venoms), prescription or non-prescription drugs, viral or bacterial exposure, trauma and the like.

The invention will now be described in more detail in the following non-limiting examples.

EXAMPLES

As briefly mentioned above, conventionally, identification of myocellular necrosis in patients with an ischemic cardiomyopathy has been performed by locating the voxels with a signal intensity >2 standard deviations above the background intensity within non-enhanced LV myocardium. The amount of necrosis is quantified by determining the transmural extent of hyperenhancement expressed as a ratio of the number of high intensity pixels extending linearly from the endocardial to the epicardial surface relative to the total distance from the endocardium to epicardium. Since myocardial necrosis proceeds in a wavefront from the endocardial to epicardial surface in the setting of reduced coronary arterial blood flow, this method is useful for assessing the amount of necrosis after myocardial infarction.

Figure 6:
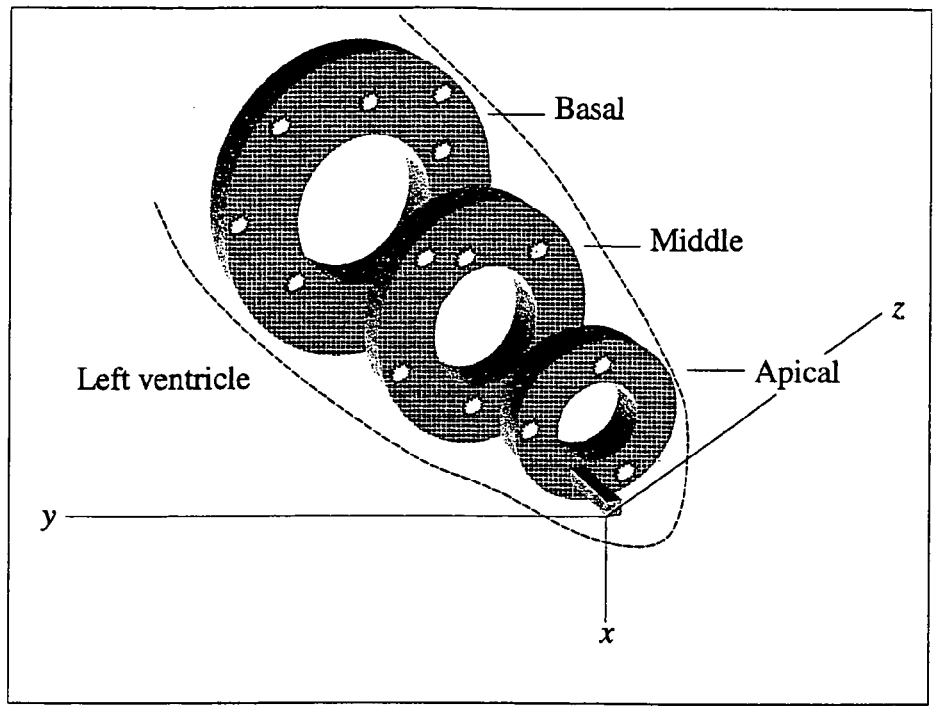
FIG. 6 is a three-dimensional depiction of three short axis planes of a left ventricle.

However, this method may not be as well suited for a process that causes necrosis to susceptible tissue throughout the LV myocardium in a randomly distributed pattern (e.g. a global injury). To overcome this limitation, voxels, and in some embodiments all the voxels, within three short axis slice positions (apex, middle, and base) within the LV may be sampled and the intensity, x, y, and z coordinates of each voxel identified in 3-dimensional space (FIG. 6). FIG. 6 is a 3-Dimensional depiction of 3 short axis (basal, middle, and apical) planes of the left ventricle. In each plane, the grid of small boxes on the face of each slice demarcate the voxels. During analysis, the image intensity of each voxel and the x, y, and z coordinates are recorded. In this way, high intensity pixels identified with the delayed enhancement technique associated with a randomly distributed process causing myocellular necrosis (white splotches on images) can be characterized.

Correction for variations in the intensity of voxels in the images may also be identified by determining the intensity of voxels within a target region, typically, a 1 cm diameter circular region of interest (ROI) placed outside the heart. For each apical, middle, and basal slice, the number of pixels at a given intensity may be determined and the intensity from the ROI external to the heart subtracted from the pixels. In certain embodiments, for each slice, the mean intensity of all voxels and the peak voxel intensity in the highest 40% of the distribution may be determined (FIG. 6). In this way, regions of high intensity pixels may be identified relative to their location within the left ventricle.

Figure 7:
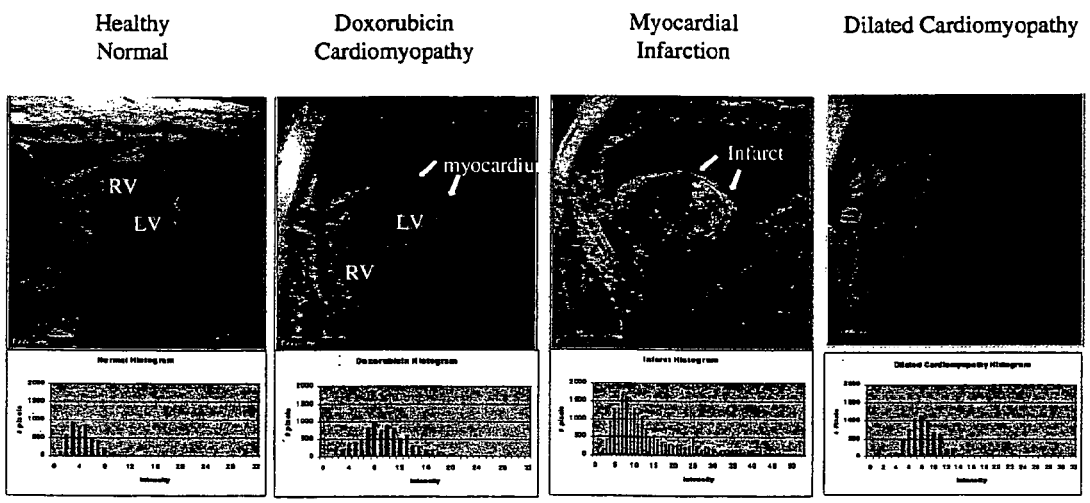
FIG. 7 is delayed enhancement MRI images in a middle (mid-plane) short axis view of the left ventricle with corresponding intensity histograms.

FIG. 7 are exemplary delayed enhancement MR images (top panels) in a middle short axis view of the LV. The myocardium is gray and the blood pool is white. The number (y-axis) and intensity (x-axis) of voxels within the ROI (redline) 20 minutes after contrast administration are displayed in the bottom panels. The contrast is taken up by all myocytes, but 20 minutes after administration, it is not cleared from necrotic cells. As shown, the mean intensity of contrast uptake is low in the healthy normal patient (far left) and highest in the patient with an infarct (third from left). An intermediate mean intensity is displayed on the histogram associated with the Doxorubicin cardiomyopathy patient (second from left).

To determine the utility of MRI assessments of the location and magnitude of gadolinium contrast uptake 20 minutes after intravenous administration, a cross-sectional study in 4 groups of age (range 35 to 50 years) and gender matched participants was performed. These included:

a) (Group I): 4 subjects (1M, 3F) without medical illness, taking no cardiac medications, and with normal LV systolic and diastolic function by MRI, b) (Group II): 3 patients (3F) without coronary arterial luminal narrowings on contrast coronary angiography but with poor LV ejection fraction (<35%) and congestive heart failure secondary to Doxorubicin administration, c) (Group III): 3 patients (2M, IF) without coronary arterial luminal narrowings on contrast coronary angiography and with poor LV ejection fraction (<35%) and congestive heart failure secondary to an idiopathic dilated cardiomyopathy, and d) (Group IV): 3 patients (2M, IF) with LV dysfunction secondary to an ischemic cardiomyopathy and prior ST-segment elevation myocardial infarction.

Figure 8:
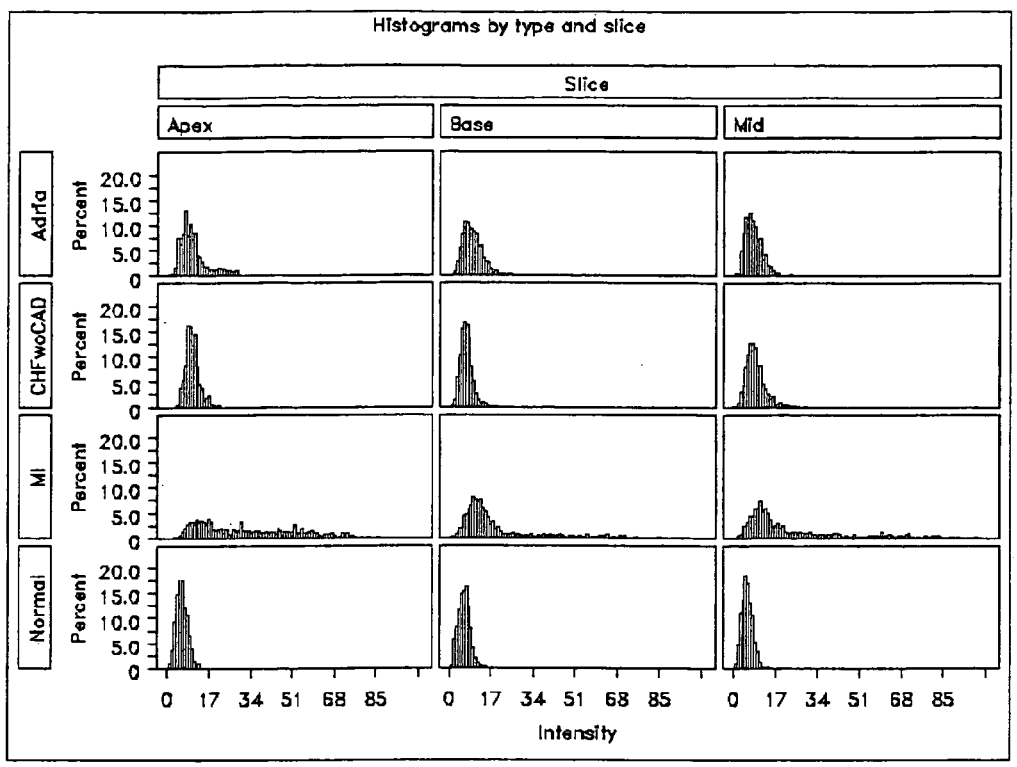
FIG. 8 is intensity histograms of voxels within a region of interest (ROI)

A middle short axis image and the distribution of intensities of voxels within the image from one subject in each group is displayed in FIG. 7, and the distributions of voxel intensities within all of the slices from all of the participants are displayed in FIG. 8.

In FIG. 8, the percentage (y-axis) and intensity (x-axis) of voxels within ROIs from all participants in the cross-sectional sampling of subjects 20 minutes after contrast administration. As displayed in FIG. 7, an increased percentage of intensities in the 15 to 30 range are displayed in patients with cardiomyopathy due to chemotherapy administration compared to normal age matched controls. This pattern of intensities appears different from that seen in patients with an ischemic cardiomyopathy.

To determine the relationship between the pattern of high intensity pixels within each slice of the left ventricle, an auto-correlation statistic was used. The serial auto-correlation measure (I) is defined as follows. Let $\delta_{ij}$ be a weighting function of the distance between pixels i and j, n be the number of pixels, and $x_i$ be the intensity for the $i^{th}$ pixel. Then define $$I = n \frac{\sum_{ij} \delta_{ij}(x_i - \bar{x})(x_j - \bar{x})}{\left(\sum_{ij} \delta_{ij}\right)\left(\sum_i (x_i - \bar{x})^2\right)}.$$ Equation (4)

I is a measure of serial autocorrelation and is higher when adjacent pixels are both higher or lower than the mean (Ripley, 1981). In practice, the expression $$\delta_{ij} = \exp\left(-\frac{1}{2}d(x_i, x_j)\right)$$

has been used, where $d(x_i, x_j)$ is the Euclidian distance between points $x_i$ and $x_j$.

Figure 9:
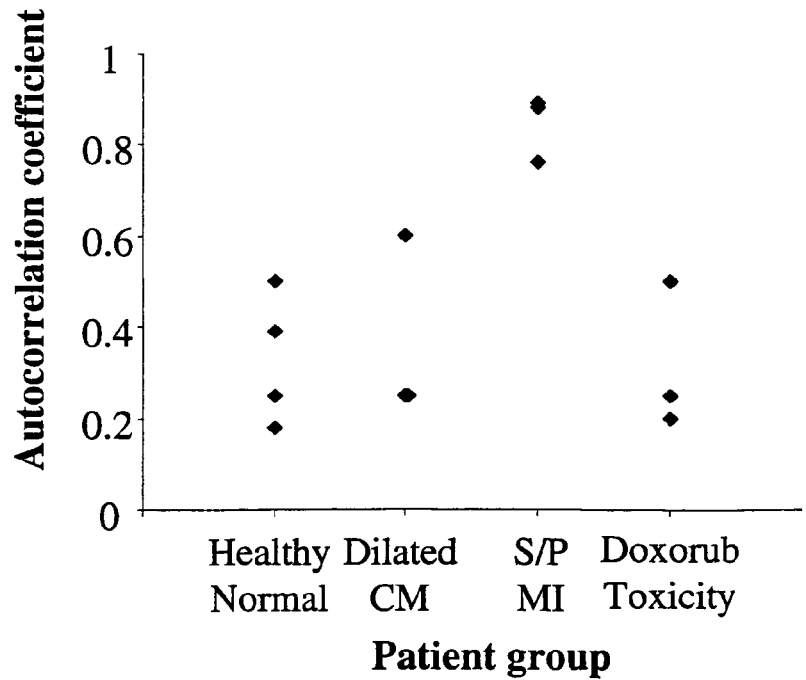
FIG. 9 is a graph of auto-correlation measures for study patients.

Using this form of analysis a high number indicates pattern clustering within the ROI, and a low number is more indicative of a random association. As shown in FIG. 9, the heightened signal intensities associated with MI were tightly clustered in the infarct zone; whereas those associated with Doxorubicin toxicity were scattered throughout the LV. The pattern of contrast uptake within the LV in patients with cardiomyopathy secondary to Doxorubicin administration was random and significantly different (p<0.001) from the pattern of high signal intensity voxels associated with myocardial necrosis secondary to myocardial infarction.

To determine if contrast enhancement is associated with a fall in LVEF in individuals receiving chemotherapy, a baseline MRI examination was performed in patients prior to initiation of chemotherapy and then additional MRI examinations were performed according to the research study protocol. Echocardiography exams were also performed to monitor patient left ventricular function between MRI examinations. One subject had developed dyspnea and received a echocardiogram to determine LVEF. The subject had a fall in LVEF from 55% to 48%. This individual underwent MRI testing and image analysis. The image analysis of this subject was compared to one other subject who had not developed a drop in LVEF during course of chemotherapy regimen. Images and the voxel intensities in the middle short axis view from the patients are displayed in FIG. 10.

Figure 10:
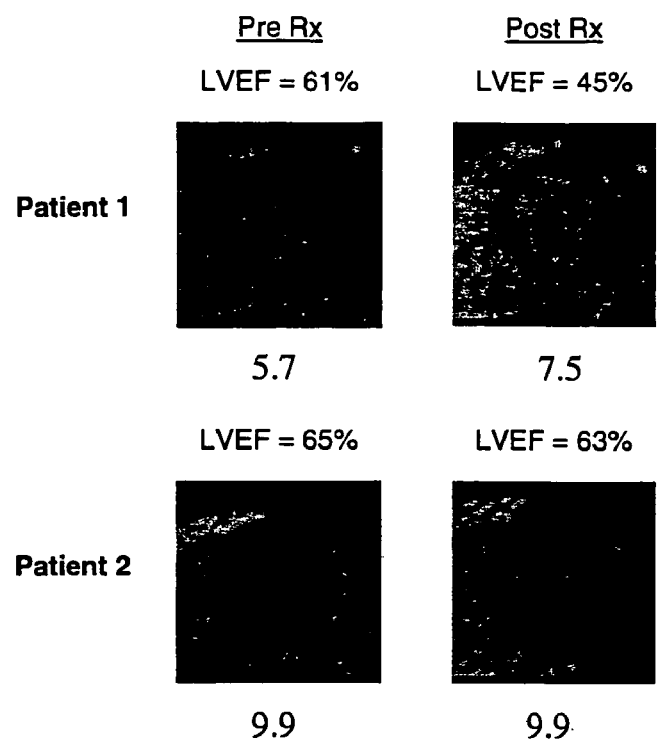
FIG. 10 are images and mean voxel intensities for two separate patients.

FIG. 10 illustrates images and mean voxel intensities at two time points in two separate patients while receiving chemotherapy, one of which developed dyspnea during the course of chemotherapy. Pre-treatment images in both patients are displayed on the left and post treatment images are displayed on the right. Mean voxel intensities for the ROI within the image are displayed under the image. In patient 1 that developed a fall in LVEF (Top panels), heightened contrast uptake and signal intensity occurred in the second exam after receipt of 400 mg/m$^2$ of anthracyclines for treatment of breast cancer. In the second patient (Bottom panels), no fall in LVEF occurred and the uptake pattern showed no significant change. As shown, in the individual with a fall in LVEF, there was a significant increase in the intensity of voxels within the LV in the second exam compared to the first, whereas in the individual without a fall in LVEF, there was no marked change on the second exam.

Figure 11:
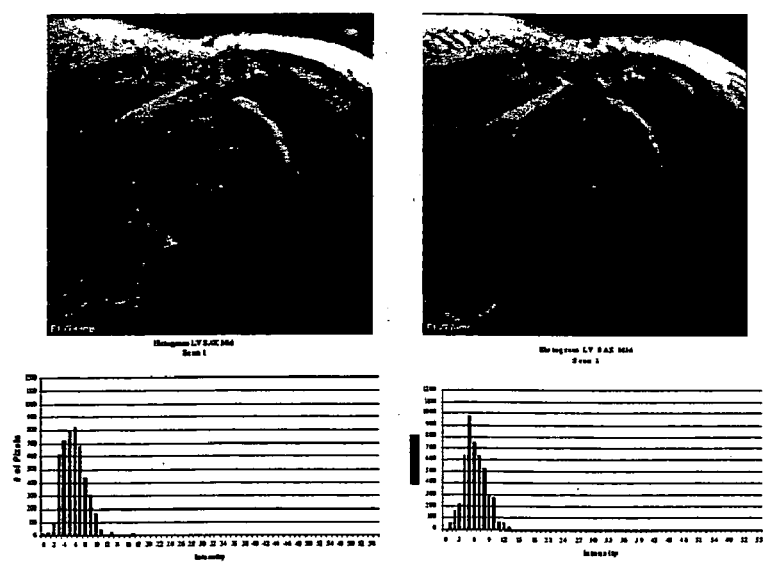
FIG. 11 are middle short axis views acquired twenty-one days apart for a patient.

To determine the variance of MRI delayed enhancement voxel intensities over time in participants without a substantive change in their medical condition, four individuals were studied twice after contrast administration over a two week period. Images from one of the participants are shown in FIG. 11, and data from both sample points in all four individuals is shown in Table 1.

TABLE 1

In four participants, MRI intensity (mean ± standard deviation) and LVEF.

|  | Day 1 | Day 21 |  |
| --- | --- | --- | --- |
| LVEF | 0.67 ± 0.04 | 0.64 ± 0.04 | p = NS |
| Mean intensity | 6.64 ± 1.15 | 6.60 ± 0.96 | p = NS |

FIG. 11 illustrates middle left ventricular short axis views acquired 21 days apart in an individual without a change in their condition. Note the near exact replication of the slice position on the second acquisition using software discussed elsewhere herein. Twenty minutes after contrast administration, the signal intensity within the ROIs was not significantly different, 5.8 versus 6.1 (p=NS). MRI examinations with this technique may be acquired reproducibly over time.

There was little change in the uptake patterns of contrast in the subjects between the first and second exam, and for the four individuals measured at two points in time, the correlation between the 2 measurements was excellent (y=0.87x+1.2, R$^2$=0.96).

Based on the above data, it appears that delayed enhancement MRI uptake patterns of contrast are elevated in patients with cardiomyopathy secondary to chemotherapy induced cardiotoxicity compared to age and gender matched control subjects. The pattern of this contrast uptake is diffuse and randomly distributed throughout the left ventricle in a fashion that is distinctly different from myocellular injury observed in patients sustaining a myocardial infarction. In the project involving two patients receiving chemotherapy, heightened contrast uptake occurred coincident with a fall in LVEF in one, but not the other that did not develop a fall in LVEF. Such a methodology and analysis methods may be highly reproducible and exhibit low intraobserver variability.

Figure 15:
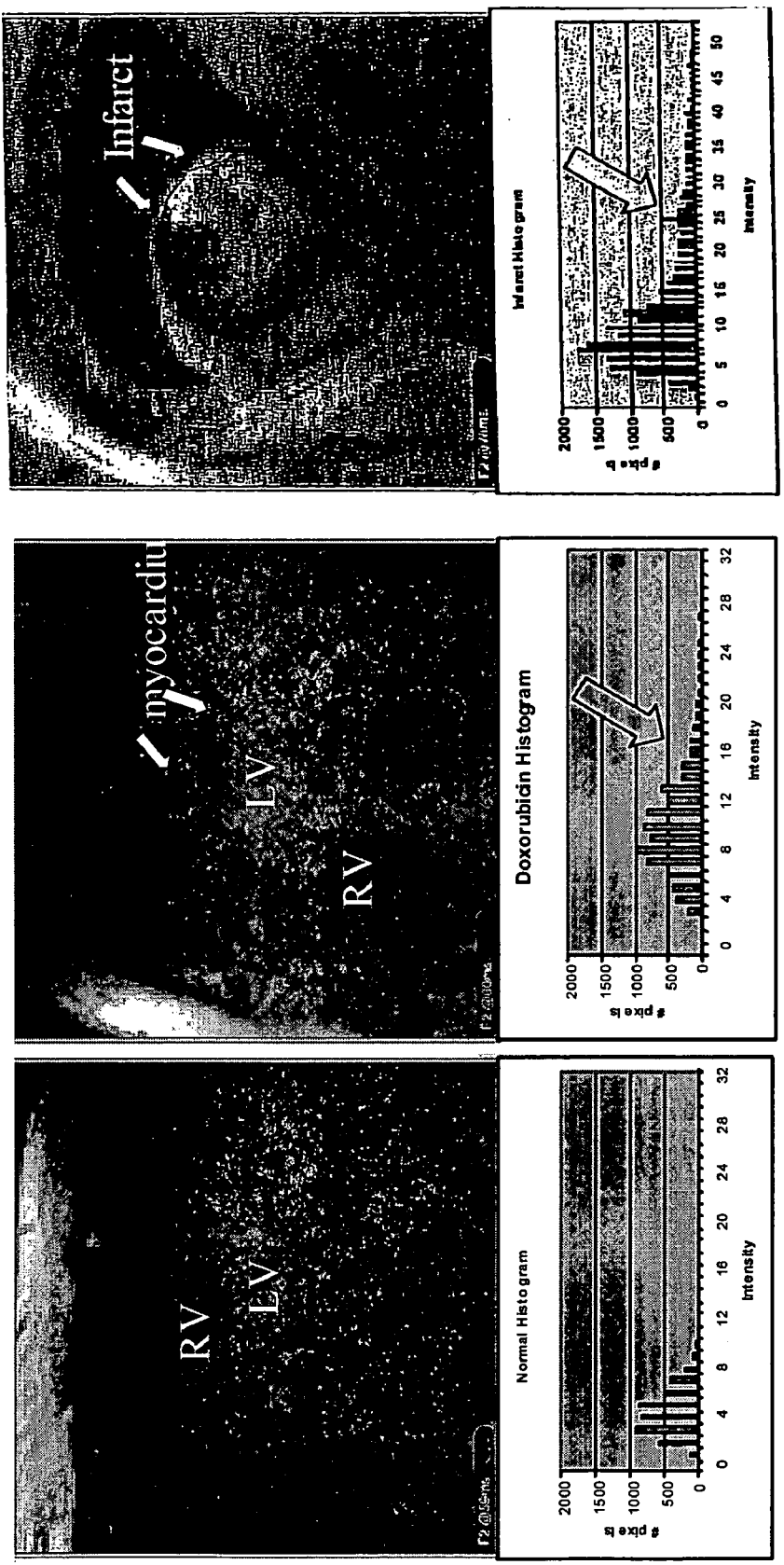
FIG. 15 are delayed enhancement CMR images in a middle (mid-plane) short axis view of the left ventricle with corresponding intensity histograms (lower panels) of number (y-axis) and intensity (x-axis) of voxels within the region of interest noted in the short axis view (top panel)

To further illustrate the utility of CMR assessments of the LV (to predict a future drop in LVEF), the location and magnitude of gadolinium contrast uptake 20 minutes after intravenous administration, a cross-sectional study in three groups of age (range 35-50) and gender matched participants. The participants included healthy subjects (Group I, n=4), patients with cardiomyopathy due to chemotherapy (Group II, n=3), and patients sustaining a prior myocardial infarction (Group III, n=3). A middle short axis image and the distribution of LV myocardial voxel intensities within the image from one subject in each group is shown in FIG. 15. Aggregate data are displayed in FIG. 16 in which the voxel intensities for the three slice positions of the left ventricle, apex, middle, and basal slice, demonstrate a similar pattern of signal intensities as shown, for example, in the middle pane of FIG. 16.

FIG. 15 shows delayed enhancement CMR images (top panels) in a middle short axis view of the left ventricle. The myocardium is gray and the blood pool is white. Beneath the images, histograms plotting the number (y-axis) and intensity (x-axis) of voxels within the region of interest on the cardiac tissue (as shown on the upper panels) delineating the LV myocardium about 20 minutes after contrast administration are displayed. The contrast is taken up by all myocytes, but at about 20 minutes after administration; it is not cleared from abnormal tissue. As shown by the arrows on the histogram, high intensity voxels are noted in the patient with doxorubicin injury and prior myocardial infarction compared to healthy "normal" patient.

Figure 16:
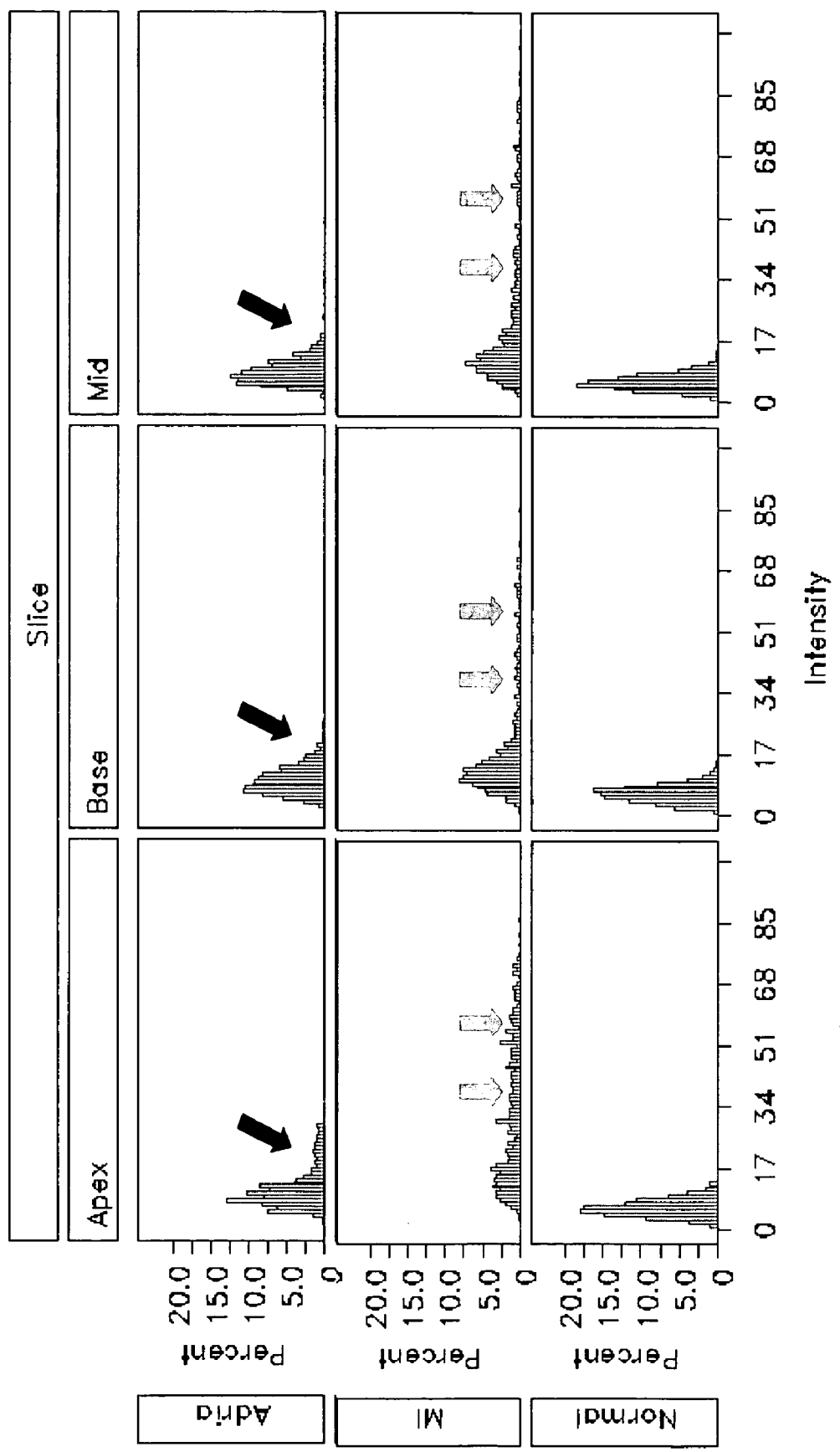
FIG. 16 are aggregate histograms graphs of percent versus intensity of voxels by type and slice according to embodiments of the present invention.

FIG. 16 illustrates aggregate histograms displaying percentage (y-axis) and intensity (x-axis) of voxels within regions of interest from all participants in the cross-sectional sampling of subjects 20 minutes after contrast administration. As displayed in FIG. 16, an increased percentage of intensities (dark arrows) are observed in patients with cardiomyopathy (labeled "Adria" in FIG. 16) due to doxorubicin administration as compared to normal age matched controls. Very high intensity voxels (lighter color or gray arrows in the mid panel histograms of FIG. 16) are noted in the slices from patients with prior myocardial infarction.

Figure 17:
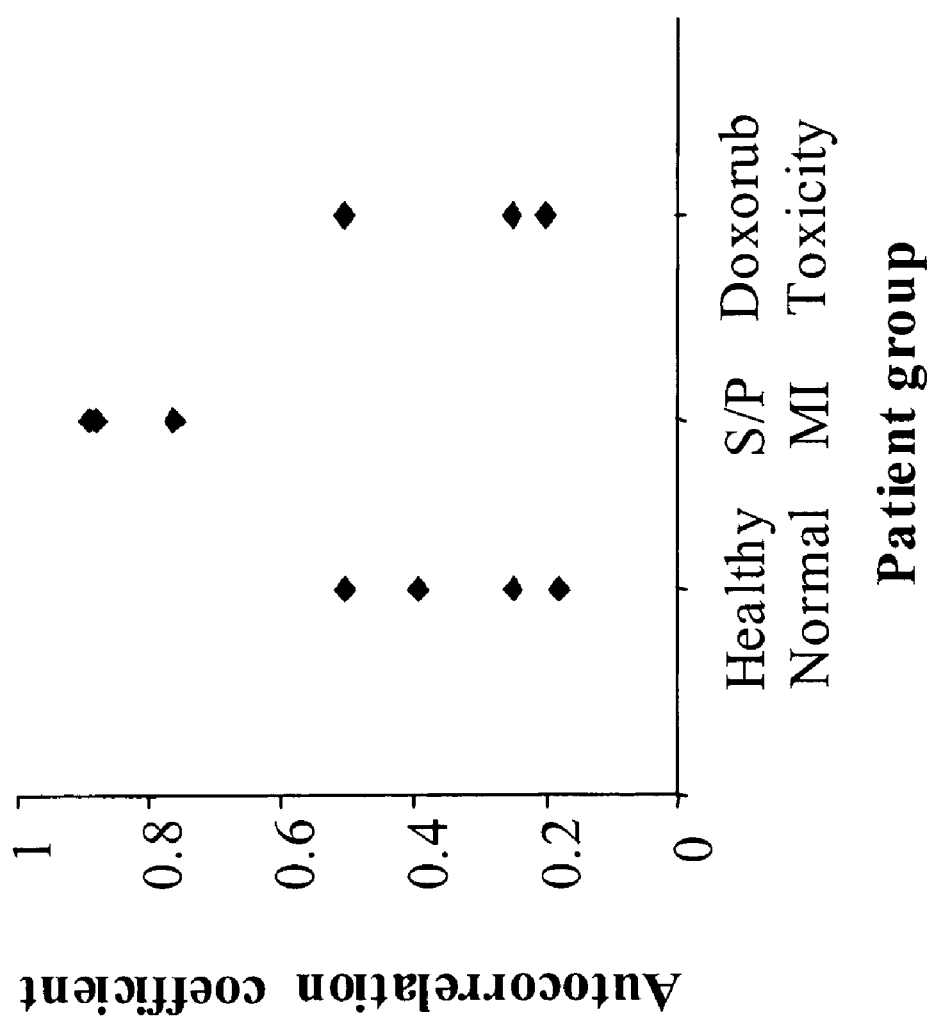
FIG. 17 is a graph of auto-correlation measures for study patients.

As discussed above with respect to FIG. 9, the relationship between the pattern of high intensity voxels within each slice of the left ventricle was determined using the correlation statistic (autocorrelation statistics). See, e.g., B. D. Ripley, *Spatial Statistics*, Wiley: NY, 1981. Using this form of analysis, a high number indicates pattern clustering of the high signal intensities within the region of interest, and a low number is more indicative of a random association. As shown in the graph of FIG. 17, the pattern of contrast uptake within the left ventricle in patients with cardiomyopathy secondary to dioxorubicin administration was random and significantly different (p<0.001) from the pattern of high signal intensity voxels associated with myocardial necrosis secondary to myocardial infarction. In addition, the pattern of high signal intensity voxels was in a distribution similar to the random pattern found in the normal individuals without myocardial injury. The serial autocorrelation measure (I) is as was discussed above with respect to FIG. 9 and Equation (4). As shown in FIG. 17, the heightened signal intensities associated with myocardial infarction were tightly clustered in the infarct zone; whereas those associated with doxorubicin toxicity were scattered throughout the left ventricle.

Figure 18:
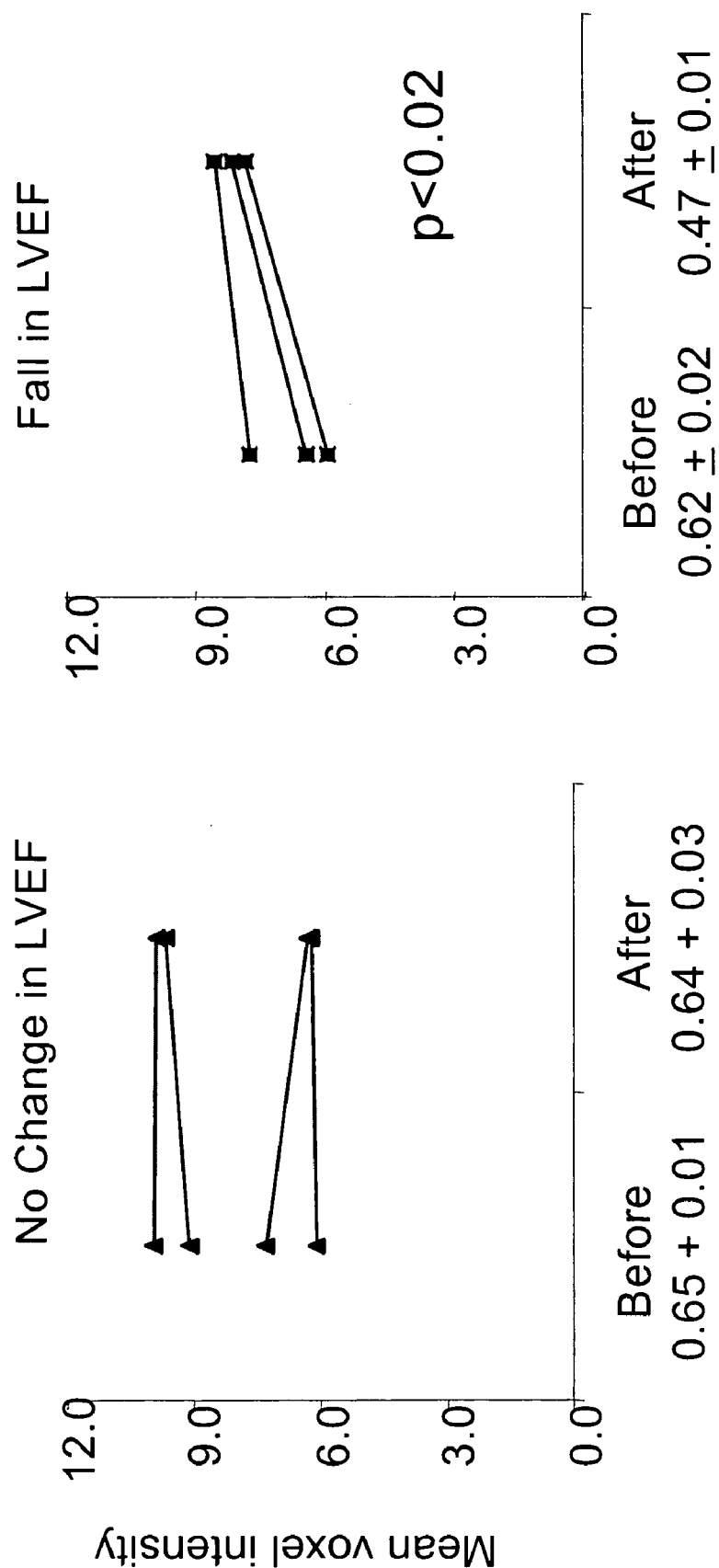
FIG. 18 are plots of mean pixel intensities of the left ventricle myocardium in a short axis plane versus LVEF before and after receipt of chemotherapy in patients without a change in LVEF (left graph) and patients that developed a fall in LVEF (right graph)

To determine if contrast enhancement is associated with a fall in LVEF in individuals receiving doxorubicin for breast cancer, a baseline CMR exam was obtained in eight patients prior to and during receipt of 2-4 months of chemotherapy. One subject died before completing the protocol. Data from the remaining seven (7) subjects is shown in FIG. 18. Three of the subjects developed a decrease in LVEF. Table 2 provides additional data regarding the time course of mean signal intensity from these patients.

FIG. 18 illustrates plots displaying the mean pixel intensities of the LV myocardium in a short axis plane before and after receipt of chemotherapy in 4 subjects without a change in LVEF (left plot) and 3 subjects that developed a decrease in LVEF (right plot). During the study, individuals receiving chemotherapy were studied at 1 month and 2-4 months after receiving chemotherapy. All subjects received doxorubicin and cytoxan in this study. Among participants that dropped and did not drop in LVEF, there was an equivalent distribution of participants receiving HERCEPTIN®, paclitaxel and 5-fluorouracil. As shown in FIG. 18, the individuals without a decrease in LVEF had no substantive increase in their mean voxel intensity during receipt of breast cancer chemotherapy. However, individuals that developed a decrease in LVEF developed a substantive increase in signal intensity on the later examinations. In participants with a drop versus those without a LVEF drop, there was a significant difference in the change in mean voxel intensity using a 2 sample t-test. The standard deviation of the mean voxel intensities over the course of the study for the four subjects without a change in LVEF was 0.64, similar to the reproducibility discussed with respect to FIG. 19 below. Table 2 provides additional data regarding the time course of contrasts intensity relative to LVEF decrement.

TABLE 2

Mean Intensity and LVEF in patients receiving chemotherapy

|  |  | Baseline | Baseline | 1 Month | 2-4 Months |
| --- | --- | --- | --- | --- | --- |
| Patient 1 | MRI | 6.4 | 8.8 | 8.1 |
|  | LVEF | 0.64 | 0.68 | 0.48 |
| Patient 2 | MRI | 6.8 | 8.1 | 8.51 |
|  | LVEF | 0.61 | 0.59 | 0.46 |
| Patient 3 | MRI | 5.9 | 7.8 | Begun on ACE |
|  | LVEF | 0.61 | 0.47 |  |

In the three subjects, the mean signal intensity of the voxels within the myocardium changed. Data was taken from these subjects before (baseline), then after receiving a chemotherapy regimen containing doxorubicin. In one individual (patient #3), the LVEF rapidly decreased at the first exam concomitant with an increase in signal intensity. In the other individuals (patient #1, patient #2), there was an increase in mean signal intensity that preceded the decrement in LVEF by about 4-8 weeks. This human subject data suggests that there is an increase in contrast uptake prior to decrement of LVEF in human subjects that develop cardiotoxicity from chemotherapy.

To determine the reproducibility of CMR delayed enhancement voxel intensities over time in patients without a substantive change in their medical condition, four individuals were studied after contrast administration over about a 2 week period. Images were analyzed in an unpaired, blinded fashion; the correlation between the two measurements was excellent ($y=0.87x+1.2$, $R^2=0.96$). To determine the reproducibility of the analysis technique, ROI's (regions of interest) were drawn twice on middle short axis images of the LV in a blinded fashion separated by a 2 month time interval. The mean intensity of the voxels was 6.38+/−0.67 on the first series of drawings and 6.35+/− on the second series. The correlation between the 2 measures of intensity analyzed on the same image set was excellent ($y=1.01x-0.1$, $R2=0.99$). A representative short axis slice from a participant in the reproducibility study is shown in FIG. 19.

Figure 19:
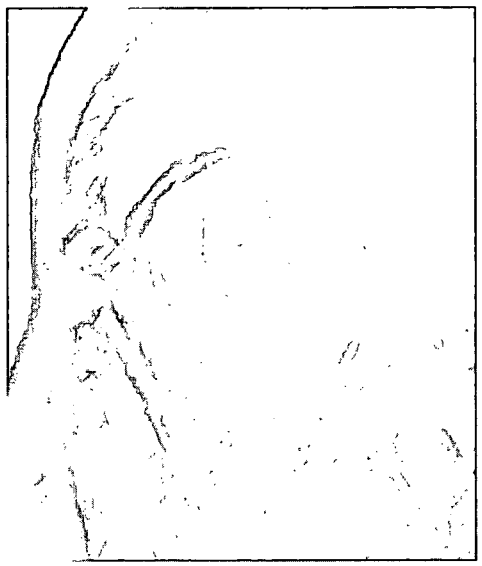
FIG. 19 are delayed contrast enhancement MRI images of middle left ventricular short axis views acquired 18 days apart in a normal individual (the anterior chest is at the top of the images) with corresponding graphs of mean voxel intensities below the respective images.
Figure 19:
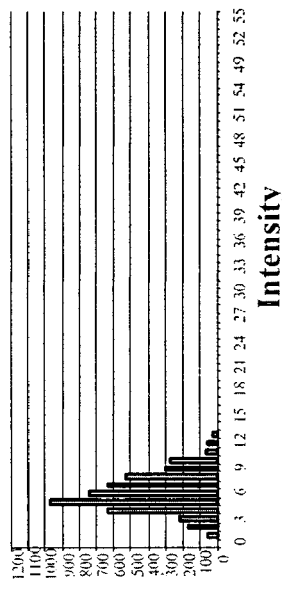
Figure 19:
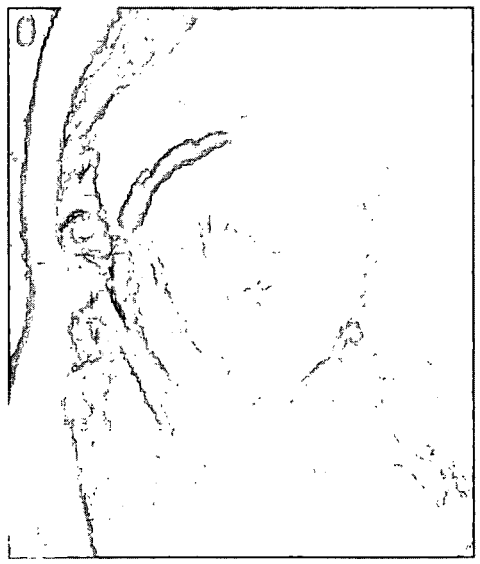
Figure 19:
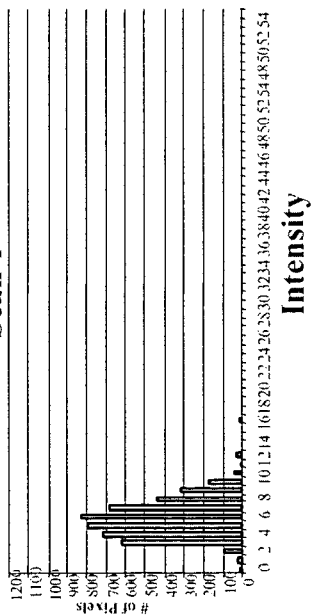

FIG. 19 illustrates middle left ventricular short axis image views acquired 18 days apart in a normal individual without a (known) change in their medical condition. The anterior chest is noted at the top of the images. In the center of the images, the LV myocardium is gray and the blood pool within the left and right ventricular cavities is generally white (or much lighter than the myocardium). Note the near exact replication of the slice position on the second acquisition using physician interactive tools that allows the physician to draw freehand, or with software GUI tools, the endo- and epi-cardial boundaries of the LV myocardium, and that can also allow a physician to define a region of interest for the background noise in the air as discussed above. About twenty minutes after contrast administration, data corresponding to the signal intensity of the voxels within the LV myocardium can be acquired as shown in the graphs beneath the images shown in FIG. 19. The signal data can be acquired, displayed, and/or stored for future or substantially concurrent (real-time) evaluation. The mean intensities (displayed beneath the graphs) were not significantly different (5.8+/−0.3 versus 6.1+/−0.3; p=NS) from one another and were highly correlated.

The statement characterizing one or more of the priority applications as a "continuation-in-part" application of a prior application listed under the "Related Applications" section above is used to indicate that additional subject matter was added to the specification of the prior application but does not necessarily mean that the entire invention described and claimed in the present application is not supported in full by the prior application(s).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims.

The invention claimed is:

1. A non-invasive method of evaluating actual and/or potential cardiac injury in a patient, comprising:
   electronically determining, for a plurality of regions of interest in a medical image of a heart, respective locations of voxels in three-dimensional space and an associated respective measure of intensity for each of the voxels;
   electronically identifying whether high intensity voxels from the determining step are clustered or distributed in the regions of interest;
   evaluating whether there is a likelihood the heart has a global injury using the measures of intensity and spatial coordinate data of the high intensity voxels based on data from the identifying step to determine whether the patient has a change in tissue composition and/or function that is in a substantially randomly distributed pattern and/or in a pattern that is not detectable at a resolution of image slices associated with the medical image; and
   providing output of the determined likelihood to a display associated with a clinician workstation.

2. A method according to claim 1, wherein the regions of interest include regions of interest derived from each of an apical, middle and basal portion of the heart.

3. A method according to claim 1, wherein the electronically identifying step comprises generating mean intensity voxel histograms, and wherein the evaluating step considers a characterizing predictive portion of the histogram that is associated with voxels having a mean intensity that is greater than 1 sigma standard deviation and less than about 3 sigma standard deviation and the three-dimensional location of those voxels.

4. A method according to claim 1, wherein the evaluating step comprises electronically assessing whether there is a clustering of voxels having an intensity that is in a range of between about 2-3 sigma standard deviation in histograms of voxel intensity whereby the 2-3 sigma standard deviation range defines a characterizing portion of the histogram.

5. A method according to claim 4, further comprising electronically identifying injury to cells in the heart prior to cell death, based on a characterizing portion of at least one of the histograms.

6. A method according to claim 1, further comprising automatically determining whether the voxels in the regions of interest are associated with an increased risk of cardiac injury associated with a decrease in heart function based on the evaluating step.

7. A method according to claim 1, wherein the evaluating step evaluates cardiac injury associated with drug-induced cardiotoxicity.

8. A method according to claim 1, further comprising generating data for a clinician to evaluate a cancer treatment therapy based on the evaluating step.

9. A method according to claim 8, wherein the generating data comprises generating data to alter, stop or decrease dosage of a chemotherapeutic agent for the patient to reduce cardiotoxicity to the patient when there is a likelihood of cardiac injury based on the evaluating step.

10. A method according to claim 1, wherein the evaluating step is carried out before a clinically relevant decrease in LVEF to thereby provide an early marker for a patient at-risk of developing irreversible cardiac injury.

11. A method according to claim 1, wherein the patient is an oncology patient, the method further comprising electronically predicting a future LVEF deterioration in the patient in response to chemotherapy.

12. A non-invasive method of evaluating actual and/or potential cardiac injury in a patient, comprising:
electronically determining, for a plurality of regions of interest in a medical image of a heart, a location of voxels in three-dimensional space and an associated respective measure of intensity for each of the voxels;
electronically generating a plurality of histograms of voxel intensity, one for each region of interest corresponding to a CMR image slice of cardiovascular tissue of the patient, the histogram having a characterizing predictive portion; and
electronically evaluating whether there is a likelihood of present or future cardiac injury based on data from the generating step,
wherein the evaluating step comprises evaluating the characterizing predictive portion of the histogram.

13. A method according to claim 12,
wherein the evaluating step comprises evaluating a line shape of the characterizing portion of the histogram, the line shape of the characterizing portion being correlated to an increased risk of cardiac injury associated with chemotherapy-induced toxicity.

14. A method according to claim 12, wherein the histogram is a histogram of a distribution of a mean intensity of voxels/pixels.

15. A method according to claim 14, wherein the regions of interest include a plurality associated with a left ventricle myocardium.

16. A method according to claim 12, wherein the characterizing portion is a tail portion of the histogram.

17. A method according to claim 16, wherein the generating data comprises generating data allowing a clinician to increase dosage of a chemotherapeutic agent when the evaluating step indicates an absence of myocellular injury.

18. A non-invasive method of evaluating actual and/or potential cardiac injury in a patient, comprising:

electronically determining, for a plurality of regions of interest in a medical image of a heart, a location of voxels in three-dimensional space and an associated respective measure of intensity for each of the voxels;
electronically evaluating whether there is a likelihood of present or future cardiac injury based on data from the determining step;
obtaining at least one cardiovascular magnetic resonance 3-D (CMR) image to generate voxel data used in the determining and evaluating steps; and
administering a chemotherapeutic agent before obtaining the at least one CMR image that is used to generate the voxel data, wherein the evaluating step is carried out to predict the likelihood of an undesired decrease in left ventricular ejection fraction (LVEF) based on a patients cardiotoxicity reaction to the administered chemotherapeutic agent.

19. A method according to claim 18, further comprising:
administering a contrast agent before obtaining the at least one CMR image; and
visually illustrating, in a compartmental model of a heart, randomly distributed regions of increased contrast uptake throughout at least a myocardium of a left ventricle.

20. A non-invasive method of evaluating actual and/or potential cardiac injury in a patient, comprising:
electronically determining, for a plurality of regions of interest in a medical image of a heart, a location of voxels in three-dimensional space and an associated respective measure of intensity for each of the voxels;
electronically evaluating whether there is a likelihood of present or future cardiac injury based on data from the determining step;
obtaining at least one cardiovascular magnetic resonance (CMR) image for the determining step medical image;
electronically generating a plurality of histograms of voxel mean intensity using voxel data from the determining step, one for each region of interest, the histograms having a tail characterizing portion; and
wherein the evaluating step comprises automatically monitoring the patient's cardiotoxicity response to chemotherapy using the characterizing portion of the histogram.

21. A method according to claim 20, wherein the characterizing portion of the histogram is associated with pixels/voxels in a region of interest that is based on substantially all of the pixels/voxels in the region of interest.

22. A non-invasive method of evaluating actual and/or potential cardiac injury in a patient, comprising:
obtaining at least one CMR image that includes a left ventricle myocardium;
electronically determining, for a plurality of regions of interest in the CMR image, a location of voxels in three-dimensional space and an associated respective measure of intensity for each of the voxels, wherein the determining step includes electronically interrogating at least substantially all voxels within a contiguous series of short axis slice positions spanning an apex to a base in the at least one CMR image and identifying the intensity and x, y and z coordinate of each voxel in three-dimensional space;
electronically generating a non-invasive biopsy image of the patient that can identify locations of voxels of similar intensities within the left ventricle using data from the determining step; and
evaluating whether there is a likelihood of present or future cardiac injury based on data from the determining step.

23. A non-invasive method of evaluating actual and/or potential cardiac injury in a patient, comprising:
- obtaining at least one CMR image that includes a right ventricle myocardium;
- electronically determining, for a plurality of regions of interest in the CMR image, a location of voxels in three-dimensional space and an associated respective measure of intensity for each of the voxels, wherein the determining step includes electronically interrogating at least substantially all voxels within a contiguous series of short axis slice positions spanning an apex to a base in the at least one CMR image and identifying the intensity and x, y and z coordinate of each voxel in three-dimensional space;
- electronically generating a non-invasive biopsy image of the patient that can identify locations of voxels of similar intensities within the right ventricle using data from the determining step; and
- evaluating whether there is a likelihood of present or future cardiac injury based on data from the determining step.

24. A non-invasive method of evaluating actual and/or potential cardiac injury in a patient, comprising:
- obtaining at least one CMR image;
- electronically interrogating at least substantially all voxels within a contiguous series of short axis slice positions spanning an apex to a base in the at least one CMR image and identifying an intensity and x, y and z coordinate of each voxel in three-dimensional space; and
- electronically generating a non-invasive biopsy image of the patient's heart that can identify locations of voxels of similar intensities within the heart for use in evaluating whether there is a likelihood of present or future cardiac injury based on data from the interrogating step.

25. A method according to claim 24, further comprising electronically adjusting the intensity of the voxels to account for background noise.

26. A non-invasive method of evaluating actual and/or potential cardiac injury in a patient, comprising:
- obtaining at least one Magnetic Resonance Imaging (MRI) image and/or X-ray Computed Tomography image of a heart of a patient;
- electronically determining, for a plurality of regions of interest in the obtained image of the heart, a location of voxels in three-dimensional space and an associated respective measure of intensity for each of the voxels;
- electronically extracting and storing x, y, and z coordinates of voxel intensity data of each voxel in a myocardium region of the at least one image;
- electronically adjusting voxel intensity data for background noise in the myocardium region;
- generating histograms of the regions of interest based on the determining step using data from the extracting and storing step; and
- electronically evaluating whether there is a likelihood of present or future cardiac injury based on data from the generating histogram step.

27. A method of predicting cardiac injury prior to an irreversible dysfunctional state, comprising:
- electronically extracting and storing x, y, and z coordinates of voxel intensity data of voxels in multiple slices of an MRI image of a left ventricle myocardium;
- electronically generating at least one histogram of mean intensities of voxels/pixels using the extracted and stored voxel data;
- electronically determining a likelihood of cardiac injury due to cardiotoxicity based on data from the at least one histogram; and
- providing output of the determined likelihood to a display associated with a clinician workstation.

28. A method according to claim 27, wherein the electronically determining step comprises distinguishing cardiac injury associated with myocardial infarct from cardiac injury associated with cardiotoxicity using data from a characterizing predictive portion of at least one histogram.

29. A method according to claim 27, wherein the electronically determining step comprises evaluating a likelihood of a future decrement in LVEF due to cardiotoxicity based on data from the histogram.

30. A method according to claim 27, wherein the determining step comprises electronically evaluating a tail portion of the histogram as a predictor of cardiotoxicity.

31. A method according to claim 27, wherein the at least one histogram is a plurality of histograms, and wherein the determining step comprises electronically evaluating the histograms to determine locations of clusters of voxels of similar intensity.

32. A signal processor circuit comprising:
- a signal processor configured to determine a likelihood of cardiac injury of a patient's heart due to cardiotoxicity using histograms of mean intensity of voxels from multiple different slices of an MRI or X-ray CT image of cardiac tissue, wherein the histograms represent percentage versus mean intensity of voxels within a region of interest, and wherein the signal processor is configured to evaluate whether the patient has a global cardiac injury using measures of mean intensity and associated spatial coordinate data of the voxels to thereby determine whether the patient has a change in tissue composition and/or function that is in a substantially randomly distributed pattern and/or in a pattern that is not detectable at a resolution of the image slices.

33. A signal processor circuit according to claim 32, wherein the signal processor is configured to evaluate a characterizing portion, distribution pattern or lineshape of the histograms to determine the likelihood of cardiac injury due to cardiotoxicity.

34. A signal processor circuit according to claim 32, wherein the signal processor is configured to distinguish cardiac injury associated with myocardial infarct from cardiac injury associated with cardiotoxicity based on a shape of a tail portion of the histograms.

35. A signal processor circuit according to claim 32, wherein the signal processor is configured to determine a likelihood of a decrement in LVEF due to cardiotoxicity based on data from at least one of the histograms to thereby allow alternative treatment protocols before irreversible cardiac injury occurs.

36. A signal processor circuit according to claim 32, wherein the signal processor is configured to evaluate a shape, lineshape or distribution pattern of a tail portion of the histogram as a predictor of cardiac injury due to cardiotoxicity.

37. A signal processor circuit according to claim 36, wherein the signal processor is configured to determine where clusters of voxels with similar intensities are located in the patients heart.

38. A non-invasive system for evaluating cardiotoxicity, comprising:
- a signal processor in communication with a physician workstation configured to generate at least one histogram of intensity voxels of at least one image of cardiac tissue of a patient and determine the likelihood of cardiac injury due to cardiotoxicity using a characterizing portion, distribution pattern or lineshape of the at least one histogram, wherein the intensity voxels are associated with an MRI or X-ray CT image of cardiac tissue, and wherein the histogram represents percentage versus a measure of intensity of voxels within a region of interest, and wherein the signal processor is configured to evaluate whether the cardiac tissue has a global injury using measures of intensity and spatial coordinate data of the voxels to thereby determine whether the patient has a change in tissue composition and/or function that is in a substantially randomly distributed pattern and/or in a pattern that is not detectable at a resolution of image slices associated with the image of cardiac tissue.

39. A system according to claim 38, wherein the at least one histogram comprises a mean intensity histogram.

40. A system according to claim 39, wherein a plurality of mean intensity histograms are generated, including histograms for a plurality of regions of interest for slice voxels associated with different axial positions of the left ventricle.

41. A signal processor circuit according to claim 38, wherein the signal processor is configured to distinguish cardiac injury associated with myocardial infarct from cardiac injury associated with cardiotoxicity.

42. A signal processor circuit according to claim 38, wherein the signal processor is configured to determine a likelihood of a decrement in LVEF due to cardiotoxicity based on data from the histogram to thereby allow alternative oncology treatment protocols before irreversible cardiac injury occurs.

43. A signal processor circuit according to claim 38, wherein the signal processor is configured to evaluate a shape, lineshape or distribution pattern of a tail portion of the histogram as a predictor of cardiac injury due to cardiotoxicity.

44. A computer program product for evaluating cardiac injury a patient's heart, comprising:
   a computer readable medium having computer readable program code embodied therein, the computer readable program code comprising:
   computer readable program code configured to determine a likelihood of cardiac injury associated with cardiotoxicity using a characterizing portion of at least one histogram of a measure of intensity of voxels in at least one cardiac image obtained after administration of a contrast agent to the patient, wherein the computer readable program code is configured to evaluate whether the cardiac injury is a global injury using the voxel measures of intensity and associated spatial coordinate data to thereby determine whether the patient has a change in tissue composition and/or function that is in a substantially randomly distributed pattern and/or in a pattern that is not detectable at a resolution of image slices associated with the at least one cardiac image.

45. A computer program product according to claim 44, further comprising computer readable program code configured to correlate voxel intensity values with x, y and z coordinates, and wherein the voxel intensity values are taken from least one CMR (Cardio Magnetic Resonance) image.

46. A computer program product according to claim 44, further comprising:
   computer readable program code configured to obtain a first image of a region of interest outside the heart corresponding to the first cardiac image;
   computer readable program code configured to correct for variations in intensity of voxels in the at least one cardiac image using the first image of a region of interest outside the heart.

47. A computer program product according to claim 44, wherein the computer readable program code configured to determine a likelihood of cardiac injury associated with cardiotoxicity is configured to distinguish cardiac injury associated with myocardial infarct from cardiac injury associated with cardiotoxicity.

48. A computer program product according to claim 44, wherein the computer readable program code configured to determine a likelihood of cardiac injury associated with cardiotoxicity comprises computer readable program code configured to determine a likelihood of a decrement in LVEF due to cardiotoxicity based on data from the histogram to thereby allow alternative oncology treatment protocols before irreversible cardiac injury occurs.

49. A computer program product according to claim 44, wherein the computer readable program code configured to determine a likelihood of cardiac injury associated with cardiotoxicity is configured to evaluate a shape, lineshape or distribution pattern of a tail portion of the histogram as a characterizing portion that is predictive of cardiac injury due to cardiotoxicity.

50. A system for non-invasively predicting cardiac injury due to cardiotoxicity prior to an irreversible state of cardiac injury associated with clinical dysfunction:
   a signal processor circuit in communication with a display at a physician workstation, the signal processor configured to electronically generate at least one histogram of mean intensity of voxels/pixels in an MRI or CT image and electronically determine a likelihood of cardiac global injury of a patient due to cardiotoxicity based on data from the at least one histogram using measures of intensity and spatial coordinate data to thereby determine whether the patient has a change in tissue composition and/or function that is in a substantially randomly distributed pattern and/or in a pattern that is not detectable at a resolution of image slices associated with the MRI or CT image.

51. A system according to claim 50, wherein the signal processor circuit comprises a statistical model that is configured to distinguish cardiac injury associated with myocardial infarct from cardiac injury associated with cardiotoxicity.

52. A system according to claim 50, wherein the signal processor circuit that is configured to electronically determine a likelihood of cardiac injury is configured to evaluate a likelihood of a future decrement in LVEF due to cardiotoxicity based on data from the histogram.

53. A system according to claim 50, wherein the signal processor circuit for electronically determining cardiac injury is configured to evaluate a tail portion of the histogram to determine the likelihood of cardiac injury due to cardiotoxicity.

54. A system according to claim 50, wherein the at least one histogram is a plurality of histograms, including a plurality of histograms for regions of interest in a left ventricle.

55. A system according to claim 50, wherein the at least one histogram is a plurality of histograms, including a plurality of histograms for regions of interest in a right ventricle.

56. A system according to claim 50, wherein the at least one histogram is a plurality of histograms, one for each of 17 different defined compartments of the heart as defined in a standardized heart model.

57. A system for non-invasively predicting injury to an organ due to toxicity:
   a clinician workstation with a display; and
   a signal processor circuit in communication with the display, the signal processor configured to: (a) identify measures of intensity of voxels of a target organ and correlate associated x, y and z coordinates of the voxels in three-dimensional space using multiple image slices of at least one imaging modality; and (b) evaluate whether the target organ has a global injury using the measures of intensity and spatial coordinate data to thereby determine whether the patient has a change in tissue composition and/or function that is in a substantially randomly distributed pattern and/or in a pattern that is not detectable at a resolution of the image slices.

58. A system according to claim 57, wherein the signal processor is configured to render a 3-D image of the organ using the identified measures of voxel intensity and correlated spatial coordinates, wherein the 3-D image visually illustrates different values of quantified voxel intensities differently so that voxels having similar measures of intensities have similar greyscale or color to visually emphasize a distribution of injured or dead cells over the organ for ease of viewability and reference for a clinician.

59. A system according to claim 57, wherein the image visually illustrates spatial locations of clusters of quantified measures of intensity of voxels having similar intensity measures, wherein clusters of similar high or low intensity pixels/voxels scattered about substantially an entire organ indicates a likelihood of present global injury or a risk of future global injury.

60. A system according to claim 57, wherein the target organ is the heart, and wherein the signal processor is configured to generate an image that illustrates randomly distributed clusters of mid-level intensity pixels/voxels in defined compartments of the heart.

* * * * *

UNITED STATES PATENT AND TRADEMARK OFFICE
CERTIFICATE OF CORRECTION

PATENT NO. : 7,747,308 B2
APPLICATION NO. : 11/346527
DATED : June 29, 2010
INVENTOR(S) : Hundley et al.

It is certified that error appears in the above-identified patent and that said Letters Patent is hereby corrected as shown below:

On Title Page:
Item (75) Inventors: Please correct "Ralph B. D'Agostino"
to read -- Ralph B. D'Agostino, Jr. --

In the Claims:
Column 30, Claim 18, Line 15: Please correct "a patients" to read -- a patient's --

Column 32, Claim 37, Line 58: Please correct "the patients" to read -- the patient's --

Signed and Sealed this

Thirtieth Day of November, 2010

David J. Kappos
*Director of the United States Patent and Trademark Office*